(12) United States Patent
Gayzik

(10) Patent No.: US 8,152,822 B2
(45) Date of Patent: Apr. 10, 2012

(54) COMBINATION THERAPY HEMOSTATIC CLIP

(75) Inventor: Caroline M. Gayzik, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 464 days.

(21) Appl. No.: 12/517,461

(22) PCT Filed: Nov. 28, 2007

(86) PCT No.: PCT/US2007/085698
§ 371 (c)(1),
(2), (4) Date: Jul. 1, 2009

(87) PCT Pub. No.: WO2008/070486
PCT Pub. Date: Jun. 12, 2008

(65) Prior Publication Data
US 2010/0016873 A1    Jan. 21, 2010

Related U.S. Application Data

(60) Provisional application No. 60/872,994, filed on Dec. 5, 2006.

(51) Int. Cl.
*A61B 17/08* (2006.01)
*A61M 5/178* (2006.01)
(52) U.S. Cl. .................... 606/151; 604/164.01
(58) Field of Classification Search .............. 606/151, 606/157, 221, 198; 604/165.01, 104; 128/830, 128/831
See application file for complete search history.

(56) References Cited

U.S. PATENT DOCUMENTS

| 943,263 A | 12/1909 | Moraweck |
| 1,510,416 A | 9/1924 | Pietz et al. |
| 1,578,800 A | 3/1926 | Brandenberger |

(Continued)

FOREIGN PATENT DOCUMENTS

DE    23 30182    6/1973

(Continued)

OTHER PUBLICATIONS

International Search Report for PCT Application No. PCT/US03/11496 dated Jul. 11, 2003.

(Continued)

*Primary Examiner* — Corrine M McDermott
*Assistant Examiner* — Christina Lauer
(74) *Attorney, Agent, or Firm* — Brinks Hofer Gilson & Lione

(57) ABSTRACT

A clip device (1612) for hemostasis includes a clip having a plurality of arms (1640, 1650) each having a proximal end and a distal end, wherein each of the arms are spaced apart from each other when the clip is in an open position and adjacent to each other when the clip is in a closed position. At least one lumen (1643, 1653) is disposed within a first of the plurality of arms and spans from the proximal end to the distal end of the first arm. At least one outlet bore is formed in the distal end of the first arm. In use, the distal ends of the plurality of arms are adapted to engage tissue in the closed position, and a sclerosing agent is adapted to be delivered to tissue via the lumen and an outlet bore formed in the first arm. Such technique facilitates treatment of the underlying bleeding using a combination of mechanical and sclerotherapy approaches.

14 Claims, 19 Drawing Sheets

U.S. PATENT DOCUMENTS

| | | |
|---|---|---|
| 2,113,246 A | 4/1938 | Wappler |
| 2,384,697 A | 9/1945 | Riccardi |
| 2,968,041 A | 1/1961 | Skold |
| 3,378,010 A | 4/1968 | Codling et al. |
| 3,518,993 A | 7/1970 | Blake |
| 3,616,497 A | 11/1971 | Esposito, Jr. |
| 3,777,538 A | 12/1973 | Weatherly et al. |
| 3,882,854 A | 5/1975 | Hulka et al. |
| 3,958,576 A | 5/1976 | Komiya |
| 4,038,987 A | 8/1977 | Komiya |
| 4,046,149 A | 9/1977 | Komiya |
| 4,169,476 A | 10/1979 | Hiltebrandt |
| 4,215,871 A | 8/1980 | Hirsch et al. |
| 4,367,746 A | 1/1983 | Derechinsky |
| 4,394,861 A | 7/1983 | Sciortino |
| 4,394,864 A | 7/1983 | Sandhaus |
| 4,446,865 A | 5/1984 | Jewusiak |
| 4,485,817 A | 12/1984 | Swiggett |
| 4,496,090 A | 1/1985 | Crevier et al. |
| 4,512,345 A | 4/1985 | Green |
| 4,681,107 A | 7/1987 | Kees, Jr. |
| 4,706,668 A | 11/1987 | Backer |
| 4,714,075 A | 12/1987 | Krauter et al. |
| 4,735,194 A | 4/1988 | Stiegmann |
| 4,759,364 A | 7/1988 | Boebel |
| 4,796,627 A | 1/1989 | Tucker |
| 4,821,721 A | 4/1989 | Chin et al. |
| 4,835,824 A | 6/1989 | Durham et al. |
| 4,841,888 A | 6/1989 | Mills et al. |
| 4,880,015 A | 11/1989 | Nierman |
| 4,887,612 A | 12/1989 | Esser et al. |
| 4,934,364 A | 6/1990 | Green |
| 4,945,920 A | 8/1990 | Clossick |
| 4,971,067 A | 11/1990 | Bolduc et al. |
| 4,983,176 A | 1/1991 | Cushman et al. |
| 5,015,249 A | 5/1991 | Nakao et al. |
| 5,049,153 A | 9/1991 | Nakao et al. |
| 5,062,848 A | 11/1991 | Frazee et al. |
| 5,100,418 A | 3/1992 | Yoon et al. |
| 5,112,343 A | 5/1992 | Thornton |
| 5,156,609 A | 10/1992 | Nakao et al. |
| 5,222,961 A | 6/1993 | Nakao et al. |
| 5,242,456 A | 9/1993 | Nash et al. |
| 5,300,081 A | 4/1994 | Young et al. |
| 5,304,183 A | 4/1994 | Gourlay et al. |
| 5,366,459 A | 11/1994 | Yoon |
| 5,395,381 A | 3/1995 | Green et al. |
| 5,441,509 A | 8/1995 | Vidal et al. |
| 5,445,167 A | 8/1995 | Yoon et al. |
| 5,464,416 A | 11/1995 | Steckel |
| 5,474,567 A | 12/1995 | Stefanchik et al. |
| 5,486,185 A | 1/1996 | Freitas et al. |
| 5,514,148 A | 5/1996 | Smith, III |
| 5,527,319 A | 6/1996 | Green et al. |
| 5,540,124 A | 7/1996 | Srhoj |
| 5,569,274 A | 10/1996 | Rapacki et al. |
| 5,601,574 A | 2/1997 | Stefanchik et al. |
| 5,634,932 A | 6/1997 | Schmidt |
| 5,695,504 A | 12/1997 | Gifford, III et al. |
| 5,700,271 A | 12/1997 | Whitfield et al. |
| 5,733,329 A | 3/1998 | Wallace et al. |
| 5,766,184 A | 6/1998 | Matsuno et al. |
| 5,766,189 A | 6/1998 | Matsuno |
| 5,782,747 A | 7/1998 | Zimmon |
| 5,895,394 A | 4/1999 | Kienzle et al. |
| 5,980,534 A | 11/1999 | Gimpelson |
| 5,989,268 A | 11/1999 | Pugsley, Jr. et al. |
| 6,001,110 A | 12/1999 | Adams |
| RE36,720 E | 5/2000 | Green et al. |
| 6,139,555 A | 10/2000 | Hart et al. |
| 6,155,968 A | 12/2000 | Wilk |
| 6,167,605 B1 | 1/2001 | Morales |
| 6,193,733 B1 | 2/2001 | Adams |
| 6,217,554 B1 * | 4/2001 | Green ................. 604/164.01 |
| 6,267,776 B1 | 7/2001 | O'Connell |
| 6,280,414 B1 * | 8/2001 | Shah et al. ................. 604/104 |
| 6,350,269 B1 | 2/2002 | Shipp et al. |
| 6,352,541 B1 | 3/2002 | Kienzle et al. |
| 6,464,710 B1 | 10/2002 | Foster |
| 6,638,297 B1 | 10/2003 | Huitema |
| 6,814,742 B2 | 11/2004 | Kimura et al. |
| 2001/0049497 A1 | 12/2001 | Kalloo et al. |
| 2002/0032462 A1 | 3/2002 | Houser et al. |
| 2002/0045909 A1 | 4/2002 | Kimura et al. |
| 2002/0055750 A1 | 5/2002 | Durgin et al. |
| 2002/0062130 A1 | 5/2002 | Jugenheimer et al. |
| 2002/0128667 A1 | 9/2002 | Kobayashi et al. |
| 2002/0133178 A1 | 9/2002 | Muramatsu et al. |
| 2002/0138083 A1 | 9/2002 | Muramatsu et al. |
| 2002/0138085 A1 | 9/2002 | Muramatsu et al. |
| 2002/0151916 A1 | 10/2002 | Muramatsu et al. |
| 2002/0173805 A1 | 11/2002 | Matsuno et al. |
| 2003/0069592 A1 | 4/2003 | Adams et al. |
| 2003/0069593 A1 | 4/2003 | Tremulis et al. |
| 2004/0092978 A1 | 5/2004 | Surti |
| 2005/0033312 A1 | 2/2005 | Suzuki |
| 2005/0080454 A1 * | 4/2005 | Drews et al. ................. 606/221 |
| 2005/0143767 A1 | 6/2005 | Kimura |

FOREIGN PATENT DOCUMENTS

| | | |
|---|---|---|
| DE | 19534320 | 2/1997 |
| DE | 298 11 510 | 6/1998 |
| DE | 100 11 292 | 8/2000 |
| DE | 102 11 049 | 3/2002 |
| EP | 0 738 501 | 10/1996 |
| EP | 1493392 | 1/2005 |
| EP | 1604614 | 12/2005 |
| WO | WO 99/20183 | 4/1999 |
| WO | WO 00/21443 | 4/2000 |
| WO | WO 03/030746 | 4/2003 |
| WO | WO 2007/011994 | 1/2007 |

OTHER PUBLICATIONS

International Search Report for PCT Application No. PCT/US03/11820 dated Jul. 11, 2003.

Partial International Search Report for PCT/US07/12754 dated Dec. 11, 2007.

International Search Report and Written Opinion for PCT/US07/85698 dated Jun. 4, 2008.

Examiner's Report for Canadian Patent Application No. 2,671,433 dated Aug. 19, 2010, 2 pgs.

* cited by examiner

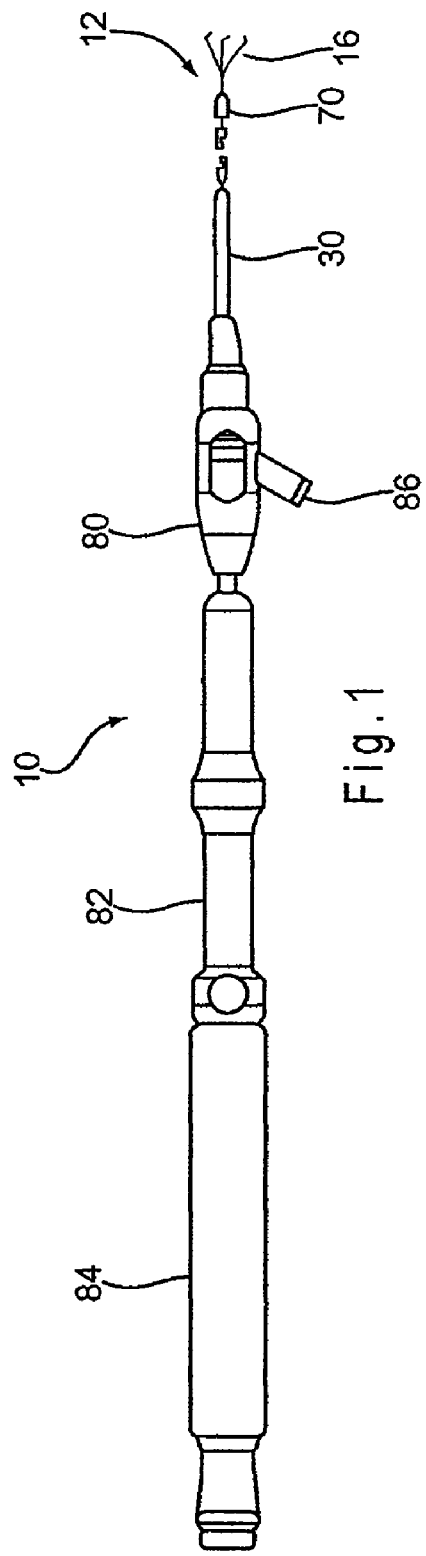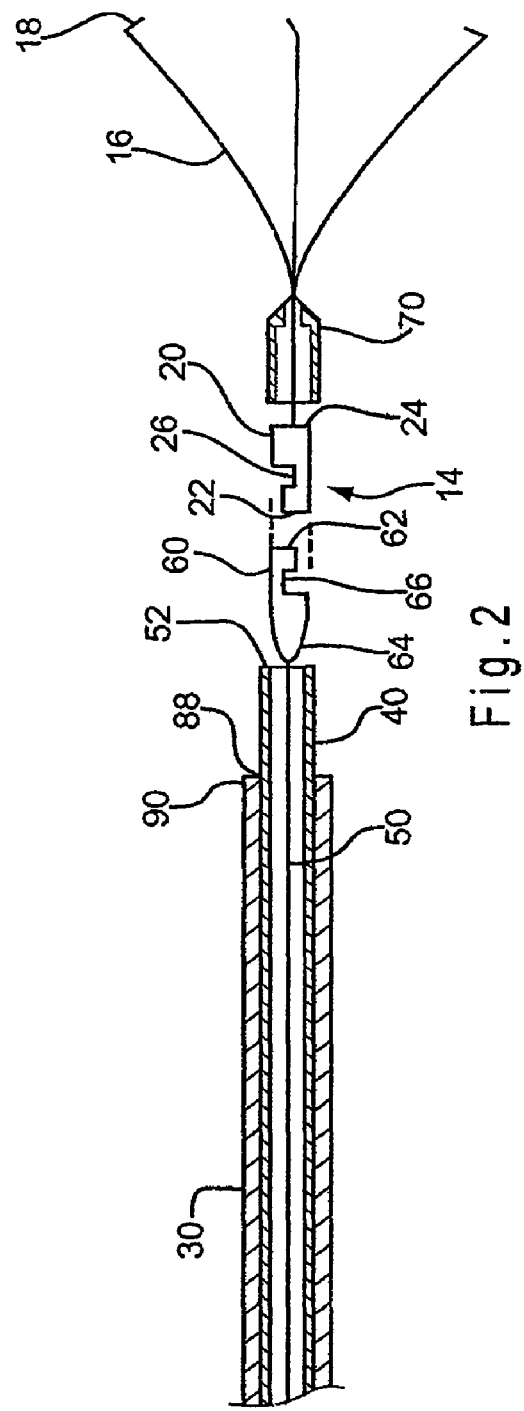

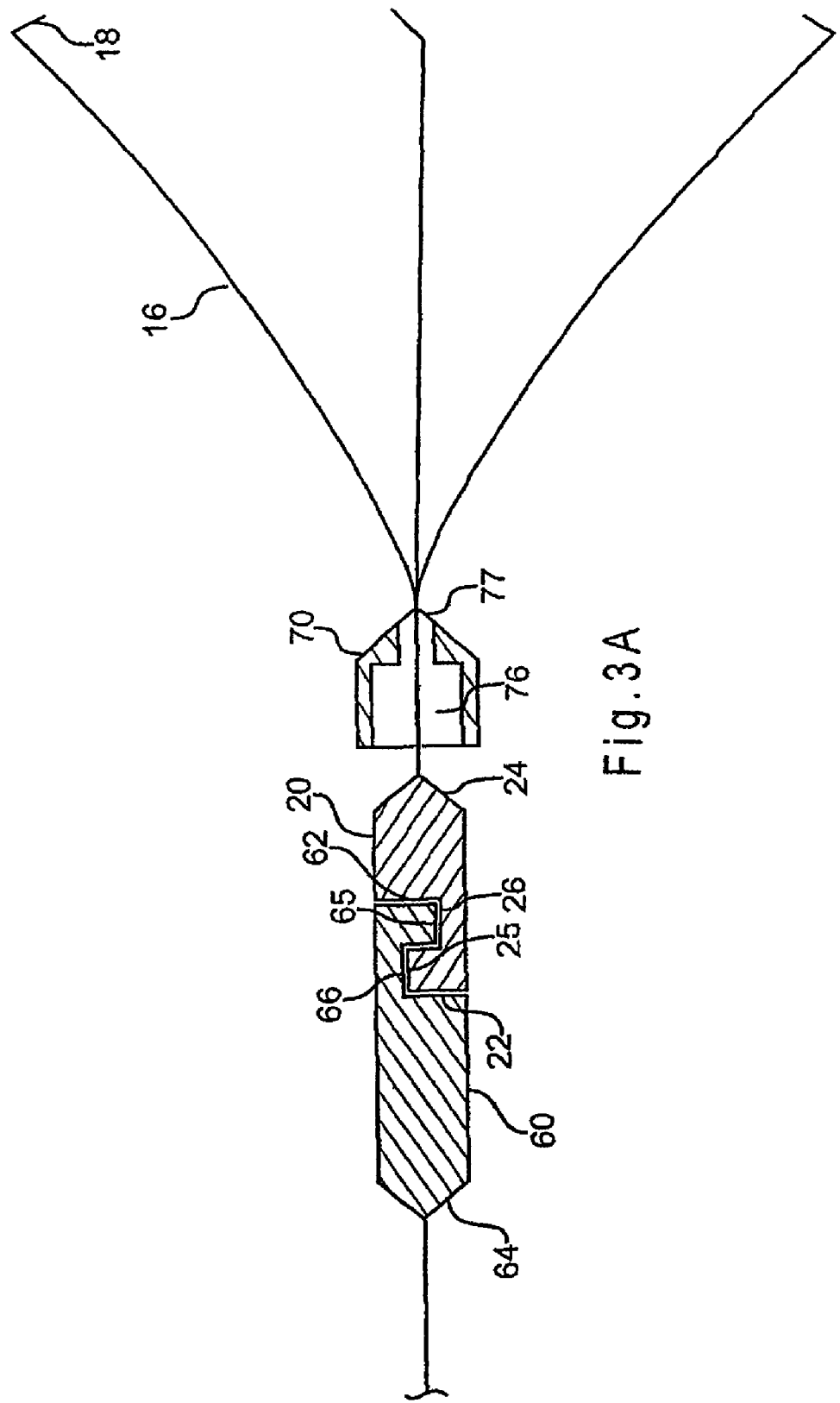

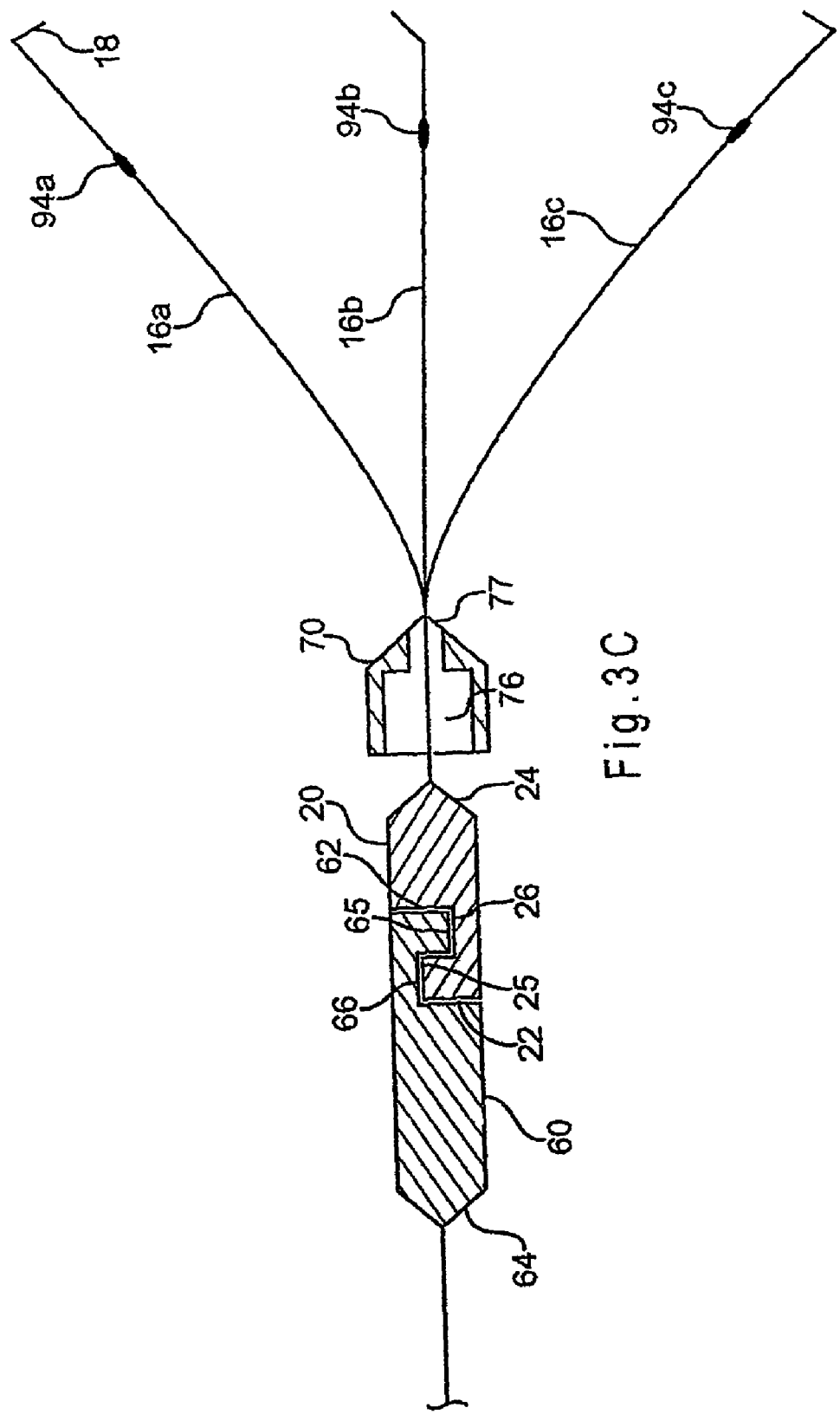

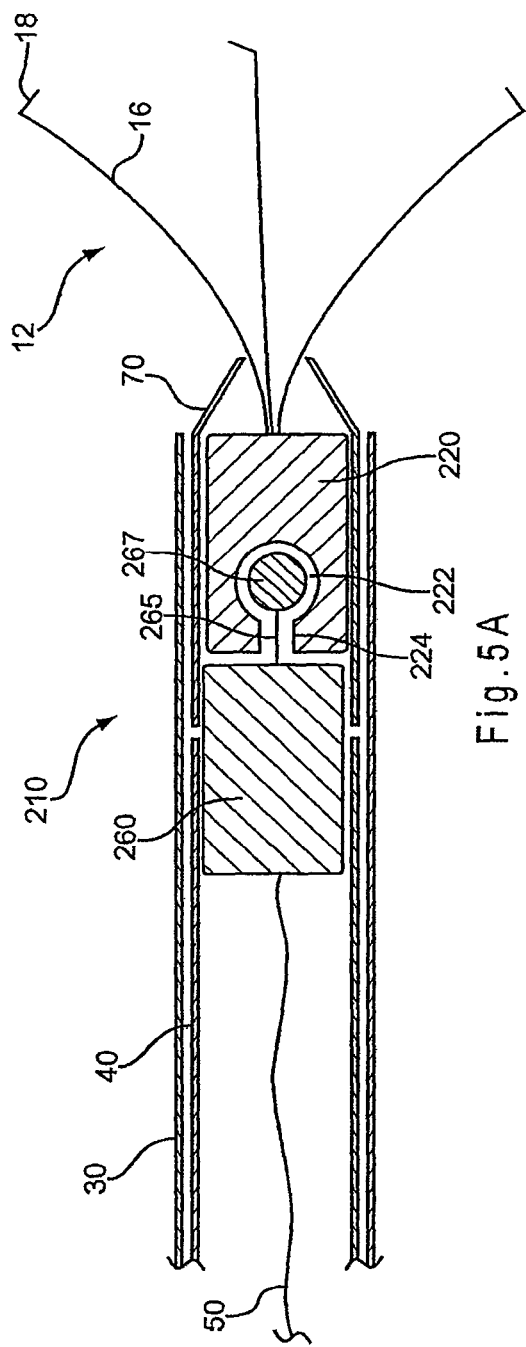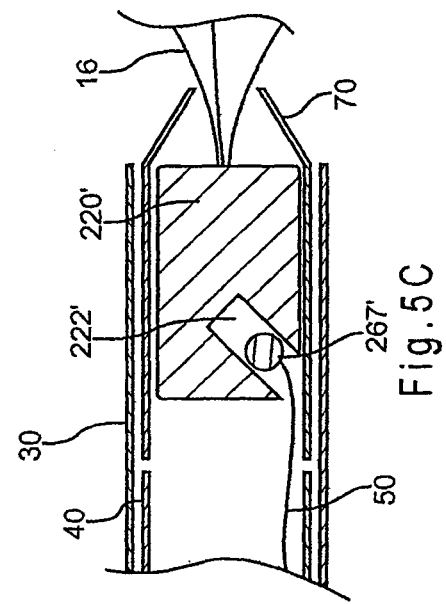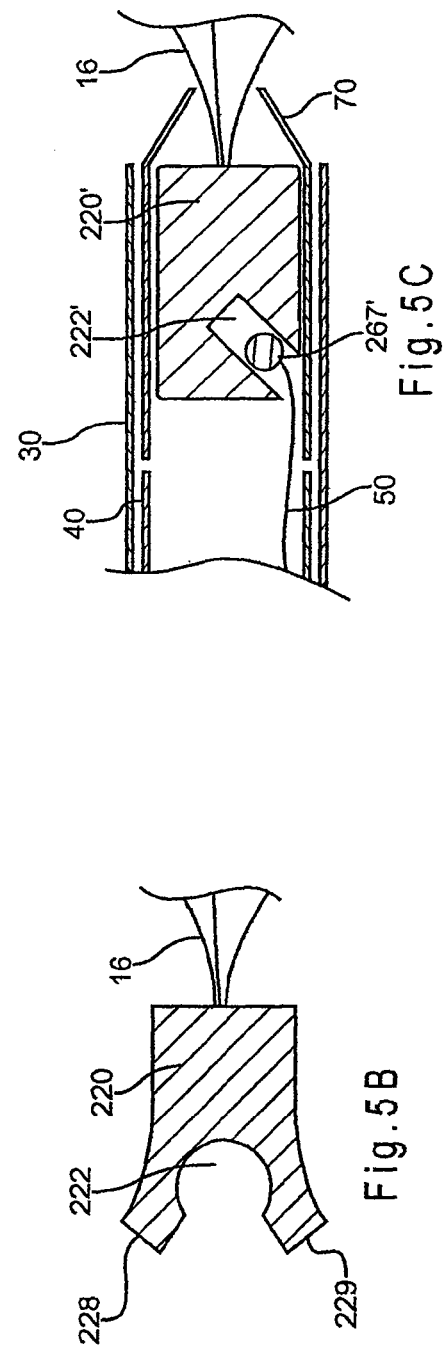

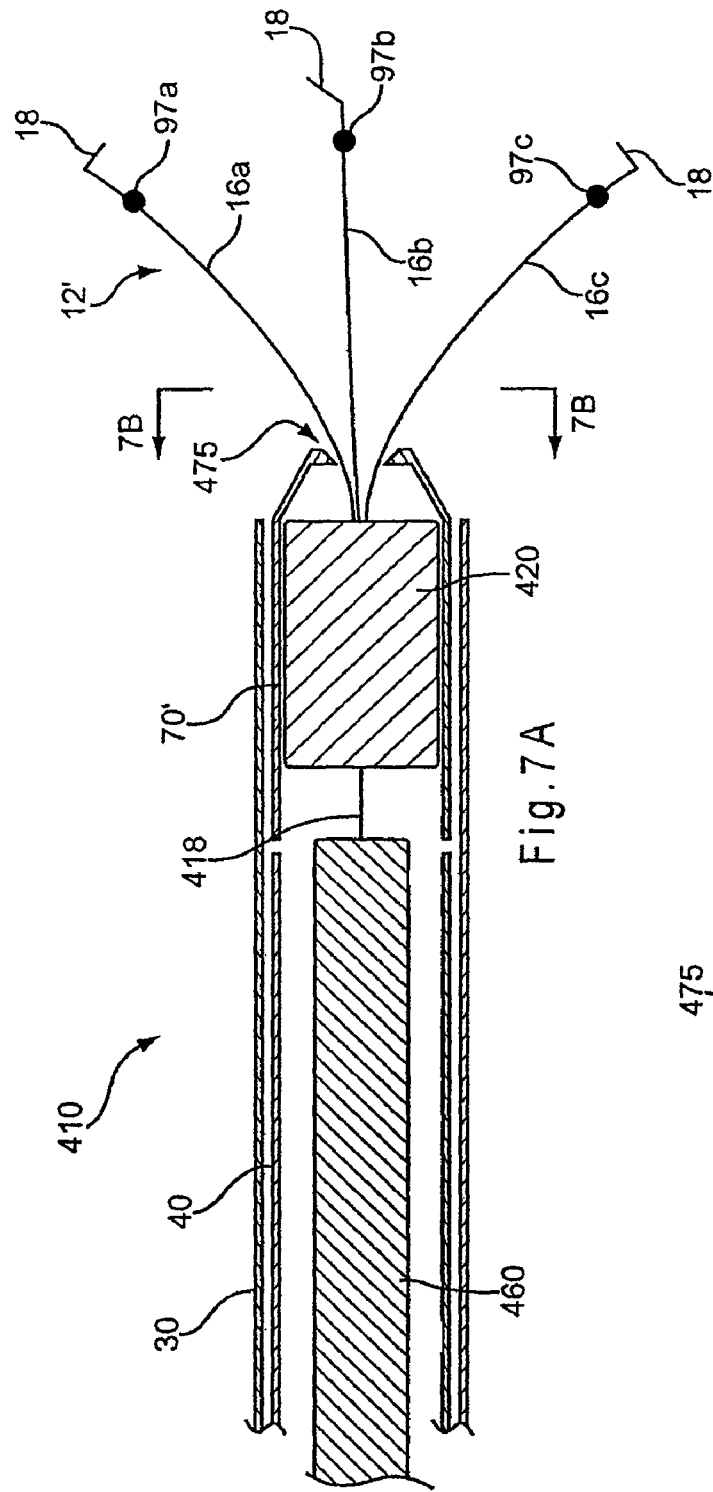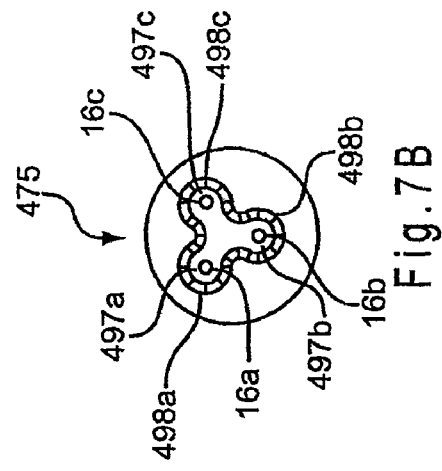

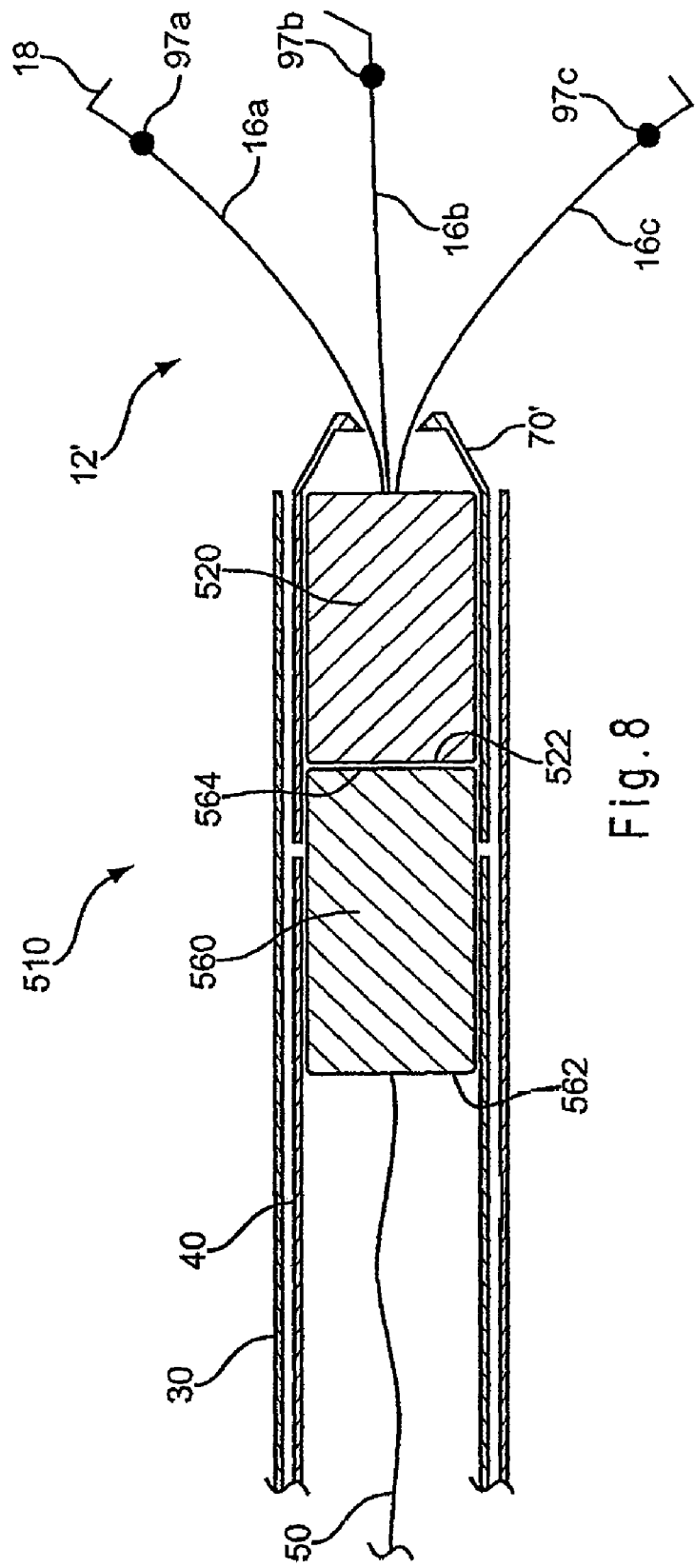

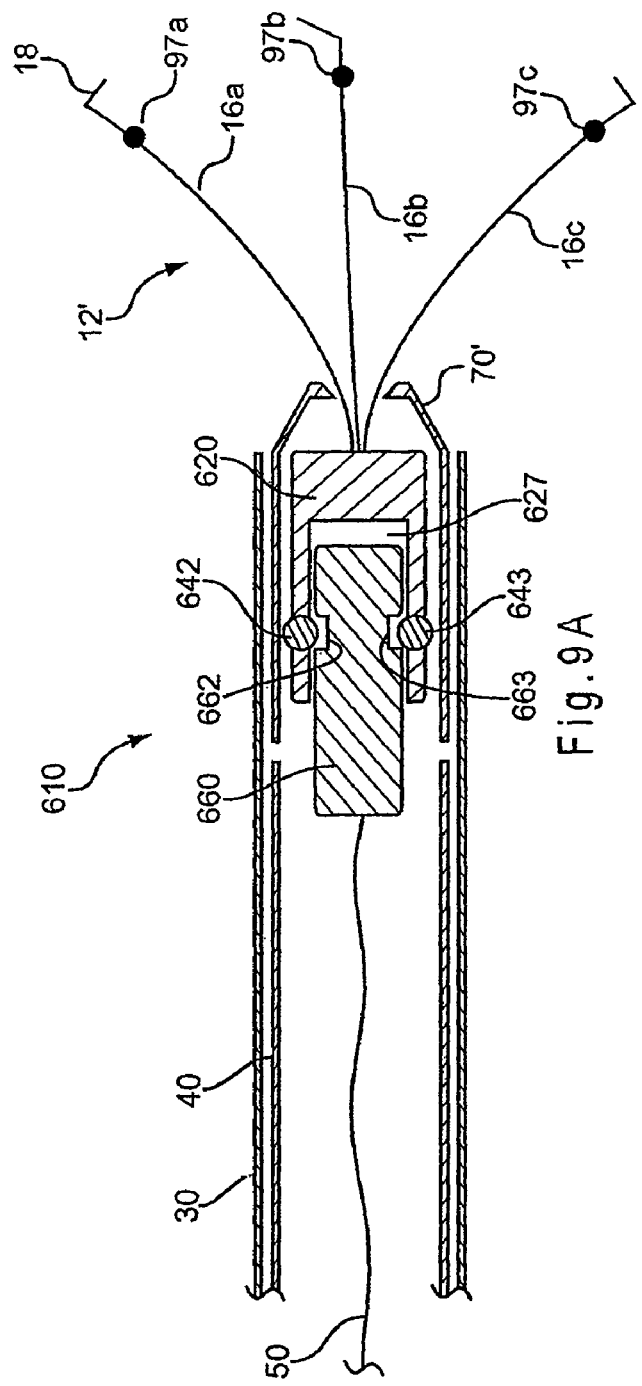
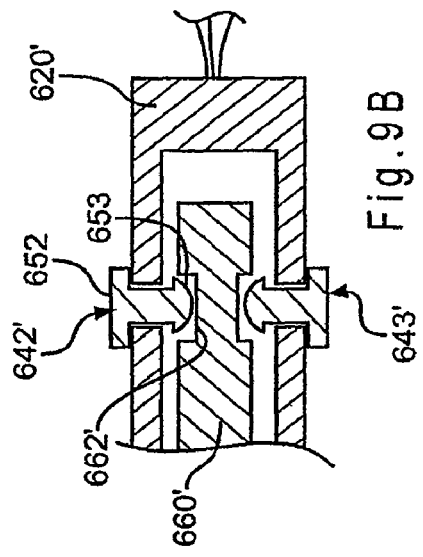
Fig. 9A
Fig. 9B

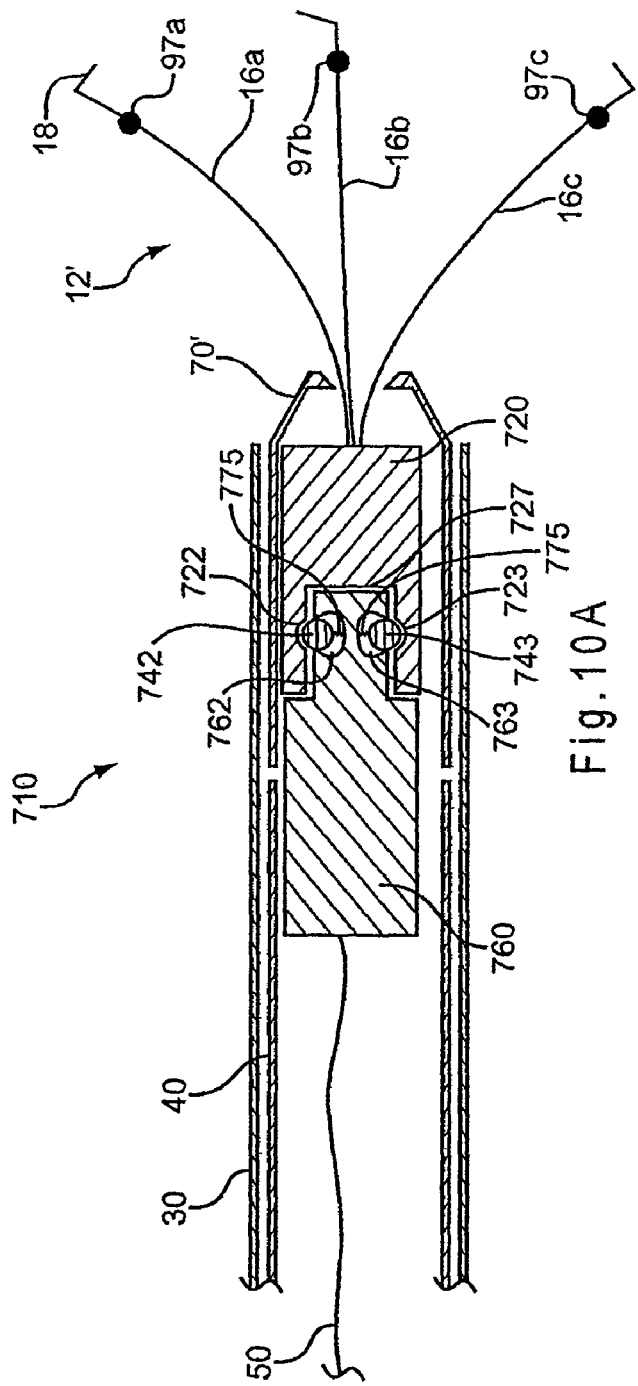
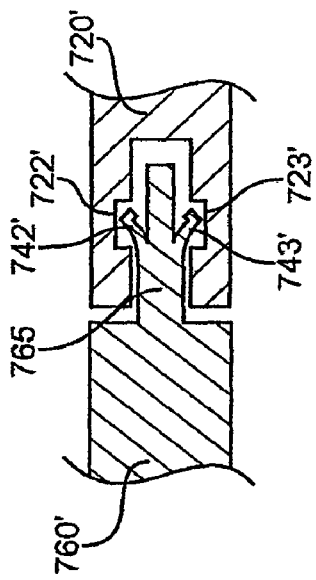
Fig. 10A
Fig. 10B

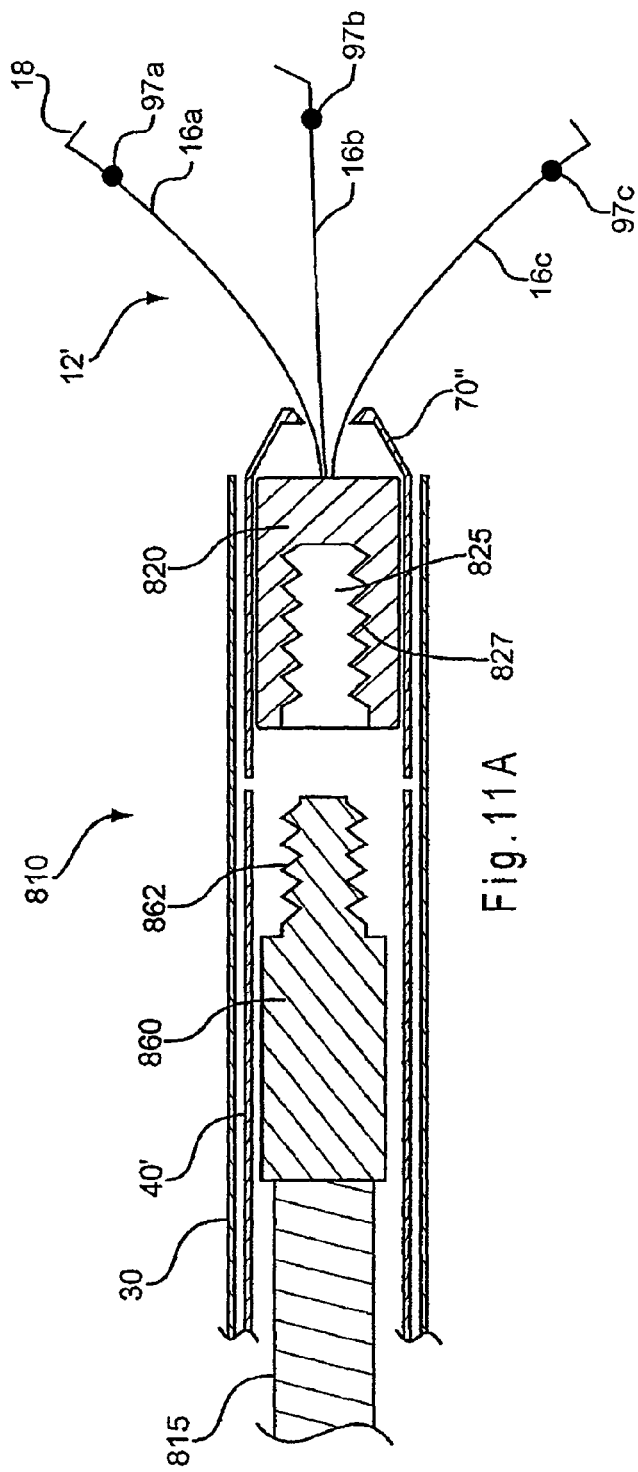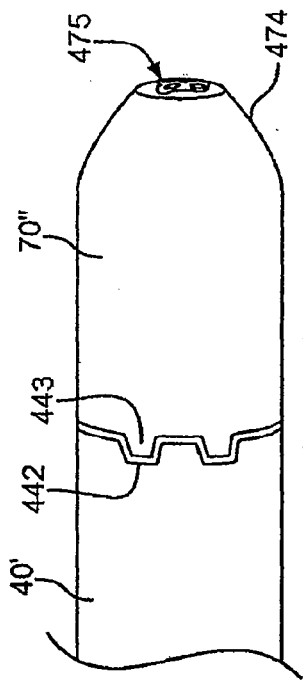

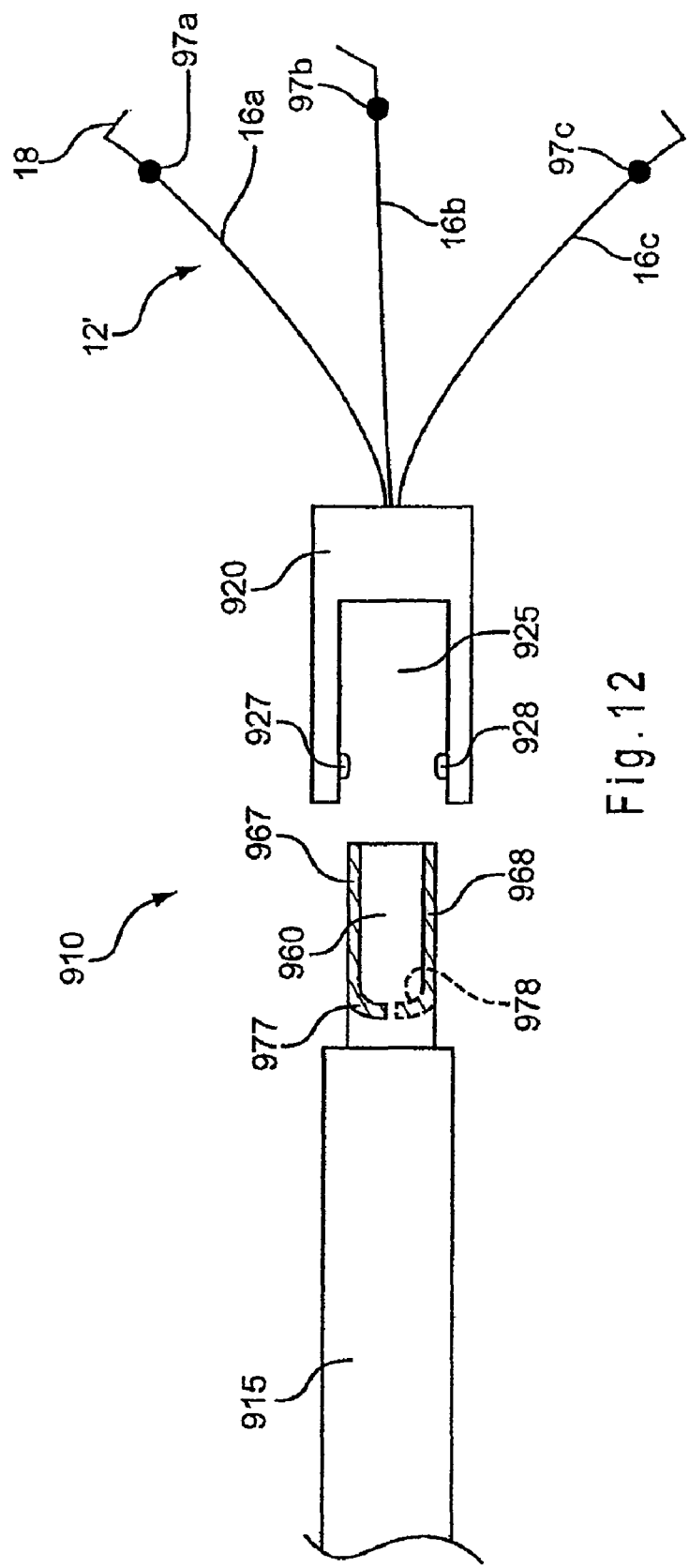

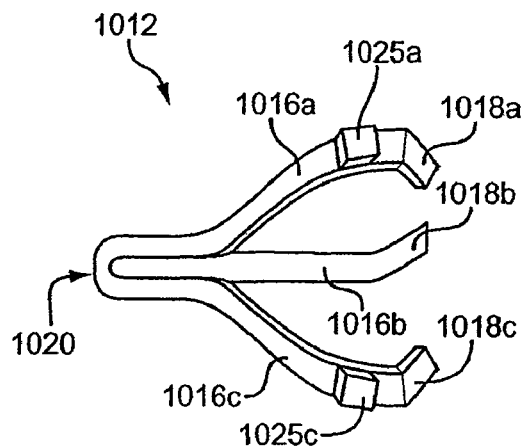
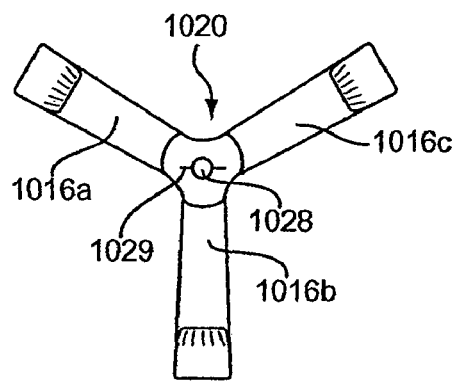
Fig.13A  Fig.13B
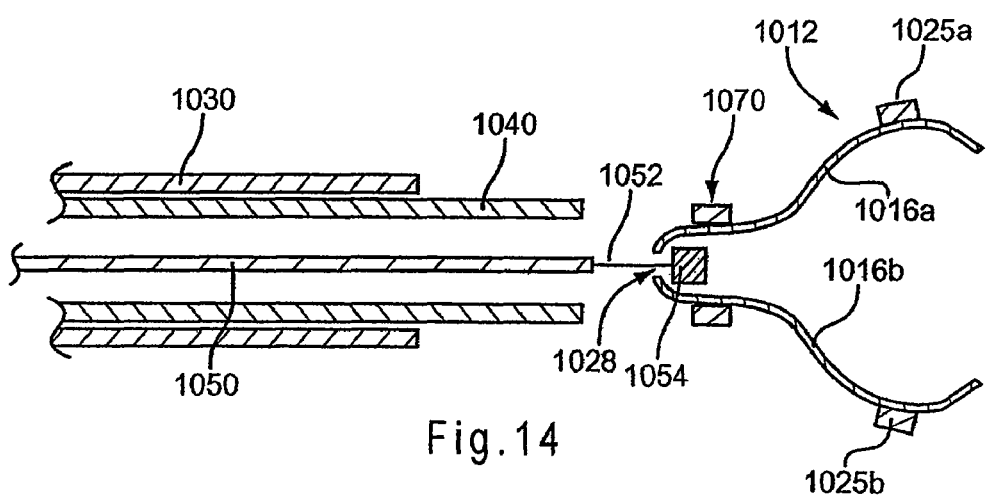
Fig.14

COMBINATION THERAPY HEMOSTATIC CLIP

RELATED APPLICATIONS

The present patent document is a §371 filing based on PCT Application Serial No. PCT/US2007/085698, filed Nov. 28, 2007 (and published as WO 2008/070486 on Jun. 12, 2008), designating the United States and published in English, which claims the benefit of the filing date under 35 U.S.C. §119(e) of Provisional U.S. Patent Application Ser. No, 60/872,994, filed Dec. 5, 2006. All of the foregoing applications are hereby incorporated by reference in their entirety.

PRIORITY CLAIM

This invention claims the benefit of priority of U.S. Provisional Application Ser. No. 60/872,994, entitled "Combination Therapy Hemostatic Clip," filed Dec. 5, 2006, the disclosure of which is hereby incorporated by reference in its entirety.

TECHNICAL FIELD

The present invention relates to a clip, and more specifically, to a clip that can be used to cause hemostasis of blood vessels along the gastrointestinal tract, or that can be used as an endoscopic tool for holding tissue or the like.

BACKGROUND INFORMATION

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples, sutures, etc. that are able to apply sufficient constrictive forces to blood vessels so as to limit or interrupt blood flow. One of the problems associated with conventional hemostatic devices, however, is that they can only be delivered using rigid shafted instruments via incision or trocar cannula. Moreover, many of the conventional hemostatic devices are not strong enough to cause permanent hemostasis.

One proposed solution is described in U.S. Pat. No. 5,766,189, which shows a clip device having a pair of arms that are provided with a tendency to open. One problem with this clip and other similar types of clips having a pair of arms is that it may often be necessary to rotate the clip to properly grasp the area to be clipped. Rotation of the clip is often hindered or complicated by the travel of the operating wire through the bends of the tube(s) used to deliver the clip. Accordingly, there is a need for a clip that can be delivered to the target area and used without having to rotate the clip to a desired orientation.

Another problem often encountered with conventional hemostatic devices is the difficulty in securing the clip device to the delivery apparatus prior to reaching the target area within the patient, and then quickly and easily releasing the clip device from the delivery apparatus once the clip has been attached to the target site.

Therefore, there is a need for a release mechanism that may quickly and reliably disengage the clip device from the delivery apparatus once the clip has been attached to the target site.

SUMMARY

A clip device for living tissue in a body cavity according to the present invention comprises an outer sheath that is insertable into the body cavity. Disposed within the outer sheath is an inner sheath. The inner sheath is independently slidable within the outer sheath. A clip is provided with a proximal end from which at least two arms extend. The arms preferably are formed of a resilient material and are shaped such that the arms are biased or have a tendency to be in an open position.

In a first embodiment, a first retainer is attached to the proximal end of the clip. An operating wire is slidably disposed within an inner portion of the inner sheath, and has a distal end portion with a second retainer attached to the distal end thereof. The second retainer releasably mates with the first retainer to couple the clip to the operating wire. A sliding ring is provided and is configured such that when the sliding ring is moved over the arms it holds them in a closed position. The sliding ring has a portion that is sized to contact the inner sheath so that when the inner sheath is advanced, the sliding ring slides over the arms of the clip to close them.

In one method of operation, the two retainers are joined together and the sliding ring is moved to a position such that the sliding ring covers the two retainers. As a result, the clip is joined with the operating wire. The outer sheath is advanced to a position over the clip to compress or collapse the arms within the device so that it may be passed into a channel of an endoscope. When the device is at the target site, the outer sheath is retracted to expose the arms, causing them to open radially outward. The inner sheath is advanced, pushing the sliding ring over the arms so as to close the arms onto the tissue. Thereafter, when the inner sheath is retracted, the retainers may be released, the device is retracted, and the clip and first retainer are left behind.

In an alternative embodiment, at least one lumen is disposed within a first of the plurality of arms of the clip. The lumen spans from the proximal end to the distal end of the first arm. At least one outlet bore is formed in the distal end of the first arm and is in fluid communication with the lumen. In use, the distal ends of the plurality of arms are adapted to engage tissue in the closed position, and a sclerosing agent is adapted to be delivered to tissue via the lumen and the outlet bore formed in the first arm, thereby facilitating treatment of the bleeding using a combined mechanical and sclerotherapy approach.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is an illustration of one embodiment of a clip device according to a first embodiment.

FIG. 2 is a partial side-sectional view of a portion of the clip device of FIG. 1 before the retainers are joined.

FIGS. 5A-5C are, respectively, a side-sectional view of an alternative release mechanism that may be used to deploy a clip device, a side-sectional view of the first retainer of FIG. 5A after deployment, and a side-sectional view of a further alternative release mechanism.

FIGS. 7A-7B are, respectively, a side-sectional view of an alternative release mechanism that may be used to deploy a clip device, and an end view showing the distal end of the sliding ring of FIG. 7A.

FIG. 8 is a side-sectional view of an alternative release mechanism that may be used to deploy a clip device.

FIGS. 9A-9B are side-sectional views of alternative release mechanisms that may be used to deploy a clip device.

FIGS. 10A-10B are side-sectional views of alternative release mechanisms that may be used to deploy a clip device.

FIGS. 11A-11B are, respectively, a side-sectional view of an alternative release mechanism that may be used to deploy a clip device, and a side view of the inner sheath and sliding ring of FIG. 11A.

FIG. 12 is a side view of an alternative release mechanism that may be used to deploy a clip device.

FIGS. 13A-13B are, respectively, a side view and a top view of an alternative clip.

FIG. 14 is a side-sectional view illustrating a method of deploying the clip of FIGS. 13A-13B.

DETAILED DESCRIPTION OF THE PREFERRED EMBODIMENTS

Figure 3B:
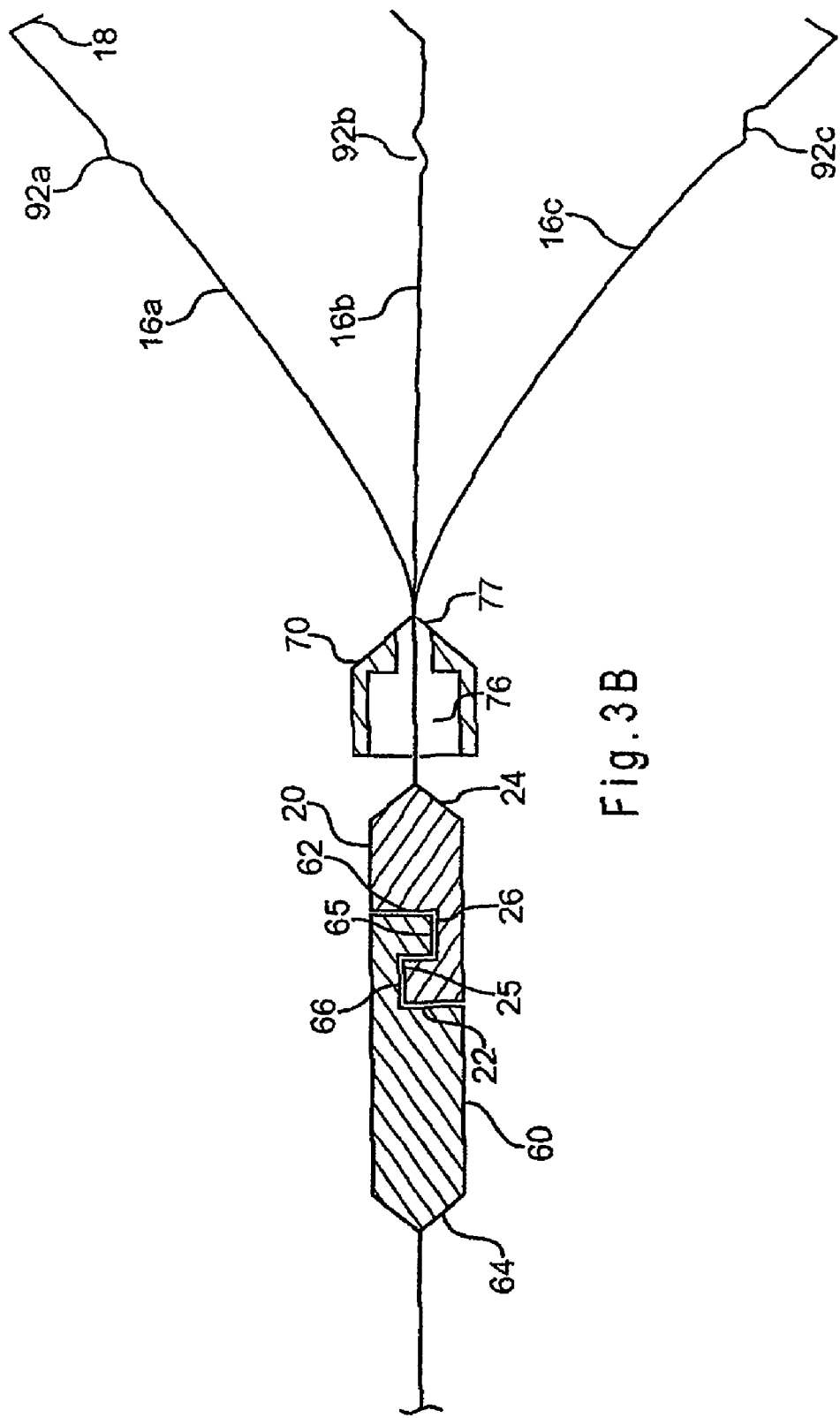
FIG. 3 is a side-sectional view of a portion of the clip device of FIG. 1 after the retainers are joined.

In the present application, the term "proximal" refers to a direction that is generally towards a physician during a medical procedure, while the term "distal" refers to a direction that is generally towards a target site within a patent's anatomy during a medical procedure.

The present invention provides a clip device for tissue or the like. Referring to FIGS. 1-3A, a first embodiment of a clip device according to the present invention is shown. Clip device 10 includes clip 12 with proximal end 14 having three arms 16 extending from the proximal end. Each arm is preferably inwardly bent at its end 18 to better grasp the tissue. While three arms are preferred, it is contemplated that fewer than or more than three arms may be used. For example, clip 12 may have two or four arms.

The clip may be made from any suitable resilient material such as stainless steel, nitinol, plastic, and the like. In addition, the arms may have a cross-sectional shape that is round, square, triangular, pie-shaped, truncated cone, and the like.

The proximal end 14 of the clip comprises first retainer 20 attached to the arms. In one embodiment, the first retainer is permanently attached to the arms. The retainer preferably is provided with a shape that will complement a shape provided on a second retainer so that the first and second retainers will matingly join with each other. For example, in the embodiment of FIGS. 1-3A, first retainer 20 has proximal end 22 and distal end 24, with notch 26 being disposed therebetween. In this embodiment, proximal end 22 approximates the shape of a half-cylinder having a flat top surface 25, as depicted in FIG. 3. As will be explained in more detail below, this shape advantageously provides secure mating with complementary second retainer 60 without increasing the diameter beyond that of the first end of the retainer.

Clip device 10 also comprises outer sheath 30 (or an introducing tube) having an inner diameter that receives inner sheath 40. The inner sheath can be advanced and retracted independently of the outer sheath. Inner sheath 40 has an inner diameter that receives operating wire 50.

Outer sheath 30 is attached at its proximal end to forward handle portion 80. Inner sheath 40 extends through forward handle portion 80 and is attached at its proximal end to middle handle portion 82, which is disposed proximally of the forward handle portion. Operating wire 50 extends through the forward and middle handle portions, and is attached at its proximal end to rearward handle portion 84, which telescopically extends over the proximal portion of the middle handle portion. As will be explained in more detail below, longitudinal movement of the operating wire and the inner and outer sheaths with respect to each other is controlled by longitudinal manipulation of the forward, middle and rearward handles portions with respect to each other.

Forward handle portion 80 preferably includes flushing port 86. The flushing port may comprise a standard male or female luer fitting, or any other valve mechanism that permits the injection of fluid therethrough. The flushing port is in fluid communication with an interior volume of forward handle portion 80, which in turn is in fluid communication with a cavity or gap 88 that is disposed between the inner and outer sheaths. Accordingly, any fluid injected through flushing port 86 will necessarily enter cavity 88 between the inner and outer sheaths, and will subsequently exit cavity 88 near distal end 90 of outer sheath 30 (see FIG. 2). In other words, the fluid injected through the flushing port will exit the clip device near the clip.

Alternatively, the cavity can be disposed inside inner sheath 40, or either the inner or the outer sheath may comprise a lumen disposed therein through which fluid can be passed along the length thereof. It should also be understood that the flushing port could be alternatively located on either of the middle or rearward handle portions, or on a portion of the outer sheath distally of any of the handle portions.

In the embodiment of FIGS. 1-3A, second retainer 60 is attached to the distal end of operating wire 50. Preferably, second retainer 60 is complementary to first retainer 20 so that the first and second retainers can be matingly joined. Accordingly, second retainer 60 has proximal end 64 and distal end 62, with notch 66 being disposed therebetween. In this embodiment, distal end 62 approximates the shape of a half-cylinder having a flat surface 65, as depicted in FIG. 3A.

The first and second retainers are joined with each other by locating flat surface 25 of first retainer 20 within notch 66 of second retainer 60, and by locating flat surface 65 of second retainer 60 within notch 26 of first retainer 20. When joined, the first and second retainers form a substantially continuous cylinder shape having substantially the same outer diameter from proximal end 64 of second retainer 60 to distal end 24 of first retainer 20, as shown in FIG. 3A.

It will be understood by one of skill in the art that, although first retainer 20 matingly joins with second retainer 60, they will not retain a joined position unless they are held together. Accordingly, sliding ring 70 is provided and has a first inner diameter 76 slightly larger than an outer diameter of first retainer 20 and second retainer 60. In other words, the first inner diameter 76 of sliding ring 70 is such that the sliding ring can slide over the retainers, yet hold and maintain them in a mating position. In addition, sliding ring 70 can slide toward the ends of arms 16 of clip 12, causing the arms to move to a closed position, as explained below.

One possible method of operation of the first embodiment will be described. Outside of the patient's body, outer sheath 30 is retracted to expose inner sheath 40, operating wire 50, and second retainer 60. Clip 12 is provided and first retainer 20 is matingly joined with second retainer 60, as described with respect to FIG. 3A above. Sliding ring 70 is placed over first retainer 20 and second retainer 60 so that they are maintained in a joined position. Sliding ring 70, having the retainers secured therein, then is disposed distal to inner sheath 40 and within outer sheath 30.

In a next step, outer sheath 30 is pushed toward the distal end of inner sheath 40 and beyond the clip, causing the arms of the clip to close. In this state, outer sheath 30 is introduced into a body cavity via a working channel of an endoscope (not shown) that has been previously inserted into the body cavity. While the body cavity is observed via the endoscope, the distal end portion of outer sheath 30 is guided to a part to be treated.

If the part to be treated is obscured by blood or other bodily fluids, then a fluid such as saline is injected through flushing port 86 on forward handle portion 80. The fluid enters the cavity or gap between inner sheath 40 and outer sheath 30, and exits the distal end of the outer sheath. The fluid floods the area so as to flush any blood or bodily fluids away from the part to be treated. The injection of fluid is continued and/or repeated as necessary during the following steps so as to keep the area free of blood and other bodily fluids.

Alternatively, a vacuum force may be applied to flushing port 86 so as to create suction within the cavity or gap between the inner and outer sheaths. This suction can be used to remove blood or other bodily fluids from the area surrounding the part to be treated.

In a next step, outer sheath 30 is retracted proximally to expose clip 12, which causes arms 16 to extend in a radially outward direction, as generally depicted. Inner sheath 40 is then advanced towards clip 12, causing sliding ring 70 to slide toward arms 16 of clip 12 and causing the arms to close, thereby grasping the tissue and facilitating tissue closure. Inner sheath 40 is then retracted and when the distal end of the inner sheath passes the first and second retainers, they detach and release from each other. Clip 12 is left inside the body cavity, holding the tissue. After disengaging the retainers, the clip operating device is removed from the channel of the endoscope.

In the embodiment illustrated, the distal opening 77 of sliding ring 70 has a second inner diameter smaller than a first diameter on first retainer 20. As a result, the sliding ring is not removable from the clip. In this embodiment, the sliding ring can be located adjacent the proximal end of the clip so that the arms are in an open position. The sliding ring can then be moved to a position toward the ends of the arms to close them.

Referring now to FIGS. 3B-3C, alternative embodiments of the clip device of FIGS. 1-3A are described. In FIG. 3B, the three arms 16a-16c of clip 12 comprise kinks 92a, 92b and 92c, respectively, which may be formed by bending or warping portions of the arms as depicted. The distal opening 77 of sliding ring 70 has a second inner diameter configured to frictionally engage kinks 92a-92c of the three arms 16a-16c. In use, sliding ring 70 slides toward the ends of arms 16a-16c of clip 12, causing the arms to move to a closed position, as explained above. Once distal opening 77 of sliding ring 70 engages kinks 92a-92c of arms 16a-16c, respectively, kinks 92a-92c preferably become wedged within distal opening 77 and limit further distal movement of sliding ring 70. In effect, kinks 92a-92c serve as distal stop elements to ensure that the sliding ring cannot pass distally over the clip.

In FIG. 3C, the three arms 16a-16c of clip 12 comprise increased diameter portions 94a, 94b and 94c, respectively. Increased diameter portions 94a-94c may have diameters slightly greater than remaining portions of arms 16a-16c. The distal opening 77 of sliding ring 70 has a second inner diameter configured to frictionally engage increased diameter portions 94a-94c of the three arms 16a-16c. In use, sliding ring 70 slides toward the ends of arms 16a-16c of clip 12, causing the arms to move to a closed position, as explained above. Once distal opening 77 of sliding ring 70 engages increased diameter portions 94a-94c of arms 16a-16c, respectively, the increased diameter portions 94a-94c preferably become wedged within distal opening 77 and limit further distal movement of sliding ring 70 to ensure that the sliding ring cannot pass distally over the clip.

Referring now to FIGS. 4-12, various alternative release mechanisms for deploying a clip device are described. In general, the release mechanisms described in FIGS. 4-12 may be used in conjunction with apparatus described in FIGS. 1-3. For example, outer sheath 30, inner sheath 40, operating wire 50, sliding ring 70, forward handle portion 80, middle handle portion 82, rearward handle portion 84 and flushing port 86 may be used in the embodiments of FIGS. 4-12. Further, clip 12 may be provided in accordance with the embodiments described above, e.g., comprising three arms 16 and preferably having an inward bend 18 at its distal end to facilitate hemostasis.

Figure 4:
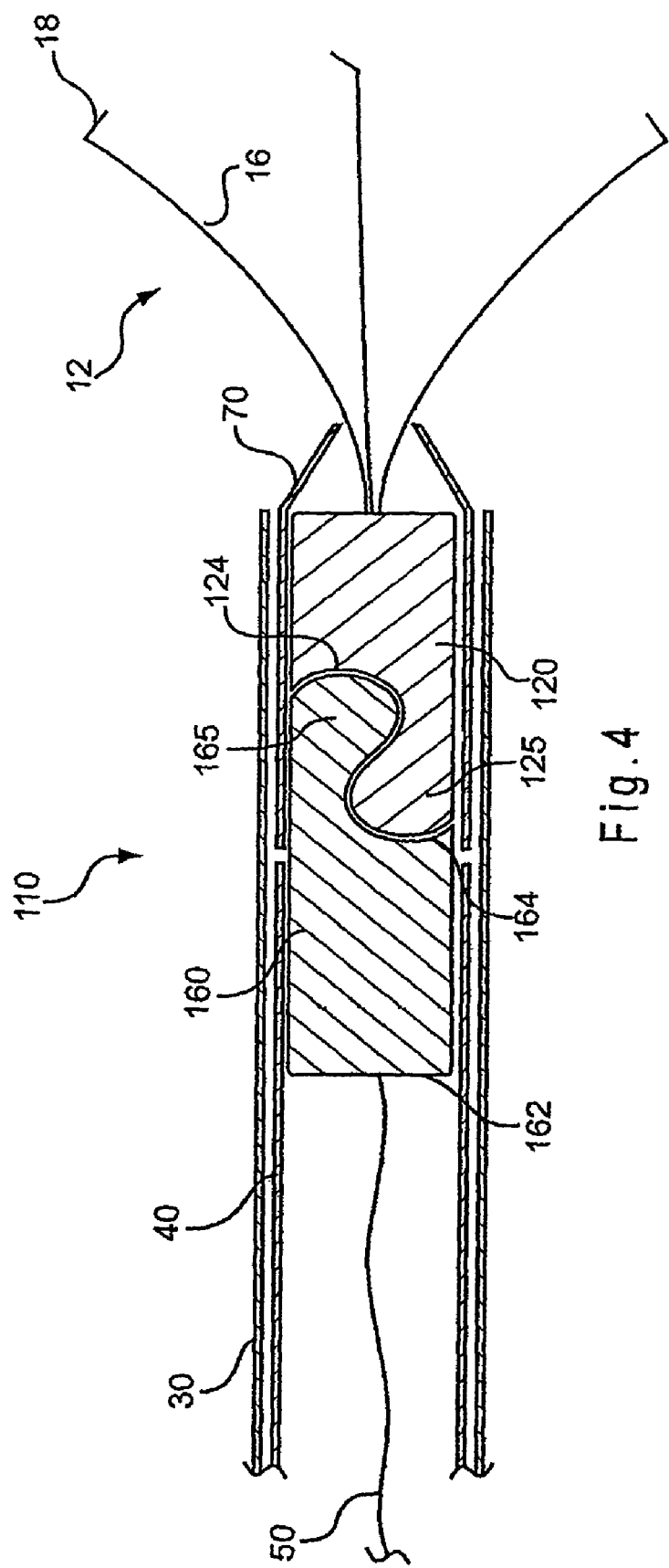
FIG. 4 is a side-sectional view of an alternative release mechanism that may be used to deploy a clip device.

Referring to FIG. 4, a first alternative embodiment for deploying clip 12 is provided. Alternative clip device 110 comprises first retainer 120 and second retainer 160. First retainer 120 is operably attached to arms 16 of clip 12. Proximal end 162 of second retainer 160 is attached to operating wire 50, as shown in FIG. 4. First retainer 120 and second retainer 160 preferably are cylindrical in cross-sectional shape and have substantially identical outer diameters when mating, as described below.

First retainer 120 comprises partially rounded notch 124 formed therein, and has rounded knob 125 formed proximal to notch 124. Similarly, second retainer 160 comprises partially rounded notch 164 formed therein, and has rounded knob 165 disposed distal to notch 164. During delivery of the device, rounded knob 165 is aligned with notch 124, while rounded knob 125 is aligned with notch 164, as shown in FIG. 4, thereby securing first retainer 120 to second retainer 160. In this embodiment, the first and second retainers are matingly held together because inner sheath 40 and/or sliding ring 70 at least partially overlaps with both retainers, thereby inhibiting movement of the retainers with respect to each other.

In operation, clip device 110 is advanced to a target site through a working channel of an endoscope (not shown). The clip device is advanced in the state depicted in FIG. 4, with the exception that outer sheath 30 is distally advanced to cover arms 16 of clip 12 to constrain the clip within the delivery device. When the desired positioning is established, outer sheath 30 is retracted proximally to expose clip 12 and permit radial expansion of arms 16, as depicted in FIG. 4. In a next step, inner sheath 40 is advanced distally to abut sliding ring 70, causing the sliding ring to be advanced distally towards clip 12 and causing the arms of clip 12 to close radially inward to grasp tissue and promote hemostasis.

In a next step, inner sheath 40 is retracted proximally past first retainer 120 and second retainer 160, thereby exposing the coupling region between the retainers. At this time, since the retainers are no longer radially constrained, they will releasably detach from one another. It is important to note that since the engaging portions of the retainers are rounded knobs, it may be less likely that the retainers will get caught on one another after deployment. First retainer 120, which is attached to clip 12, remains inside the body. Second retainer 160, which is attached to operating wire 50, is retracted via the operating wire.

Referring now to FIGS. 5A-5C, further alternative embodiments for releasably securing and deploying clip 12 are provided. Clip device 210 comprises first retainer 220 and second retainer 260. First retainer 220 is operably attached to arms 16 of clip 12, while second retainer 260 is attached to the distal end of operating wire 50, as generally described above. Further, first retainer 220 has socket 222 formed therein, which preferably comprises a hole formed laterally therethrough. Channel 224 is disposed between socket 222 and the proximal end of first retainer 220, as shown in FIG. 5A.

First retainer 220 further comprises proximal arms 228 and 229, through which channel 224 extends. In a preferred embodiment, proximal arms 228 and 229 have a relaxed or biased state in which they are bowed radially outward, as shown in FIG. 5B. In this state, channel 224 is significantly opened.

Second retainer 260 has wire 265 coupled to its distal end, and further comprises ball 267 attached to wire 265, as shown in FIG. 5A. During delivery of the device, wire 265 fits within channel 224, while ball 267 fits within socket 222, as depicted in FIG. 5A. Therefore, first retainer 220 is coupled to second retainer 260. The first and second retainers are securely held together because inner sheath 40 and/or sliding ring 70 at least partially overlaps with both retainers, thereby inhibiting outward movement of the retainers, and in particular, proximal arms 228 and 229 of first retainer 220.

Clip device 210 is advanced to a target site through a working channel of an endoscope, as generally described above. During deployment, outer sheath 30 is retracted proximally to expose clip 12 and permit radial expansion of arms 16, as shown in FIG. 5A. Inner sheath 40 then is advanced distally to abut sliding ring 70, causing the sliding ring to be advanced distally towards clip 12 and causing the arms of clip 12 to close inward to grasp tissue and promote hemostasis, as described above. In a next step, inner sheath 40 is retracted proximally past first retainer 220 and second retainer 260, thereby exposing the coupling region between the retainers. At this time, since proximal arms 228 and 229 are no longer radially constrained, they assume the configuration shown in FIG. 5B and permit ball 267 to detach from socket 222. First retainer 220, which is attached to clip 12, remains inside the body, while second retainer 260 is retracted via operating wire 50. In an alternative embodiment, second retainer 260 is eliminated and ball 267 is connected directly to operating wire 50.

In a further alternative embodiment, and as illustrated in FIG. 5C, first retainer 220' comprises angled channel 222' formed therein. Angled channel 222' may be formed partially through first retainer 220', or bored all the way through. Preferably, angled channel 222' is formed partially through the proximal end of first retainer 222', thereby forming a space through which operating wire 50 may extend. The distal end of operating wire 50 is coupled to ball 267', which is captured within channel 222' when covered by inner sheath 40 or sliding ring 70, as depicted in FIG. 5C. Once sliding ring 70 is advanced distally and/or inner sheath 40 retracted proximally, operating wire 50 may be retracted proximally and ball 267' will exit the proximal end of angled channel 222' to disengage the clip from the delivery apparatus.

Figure 6:
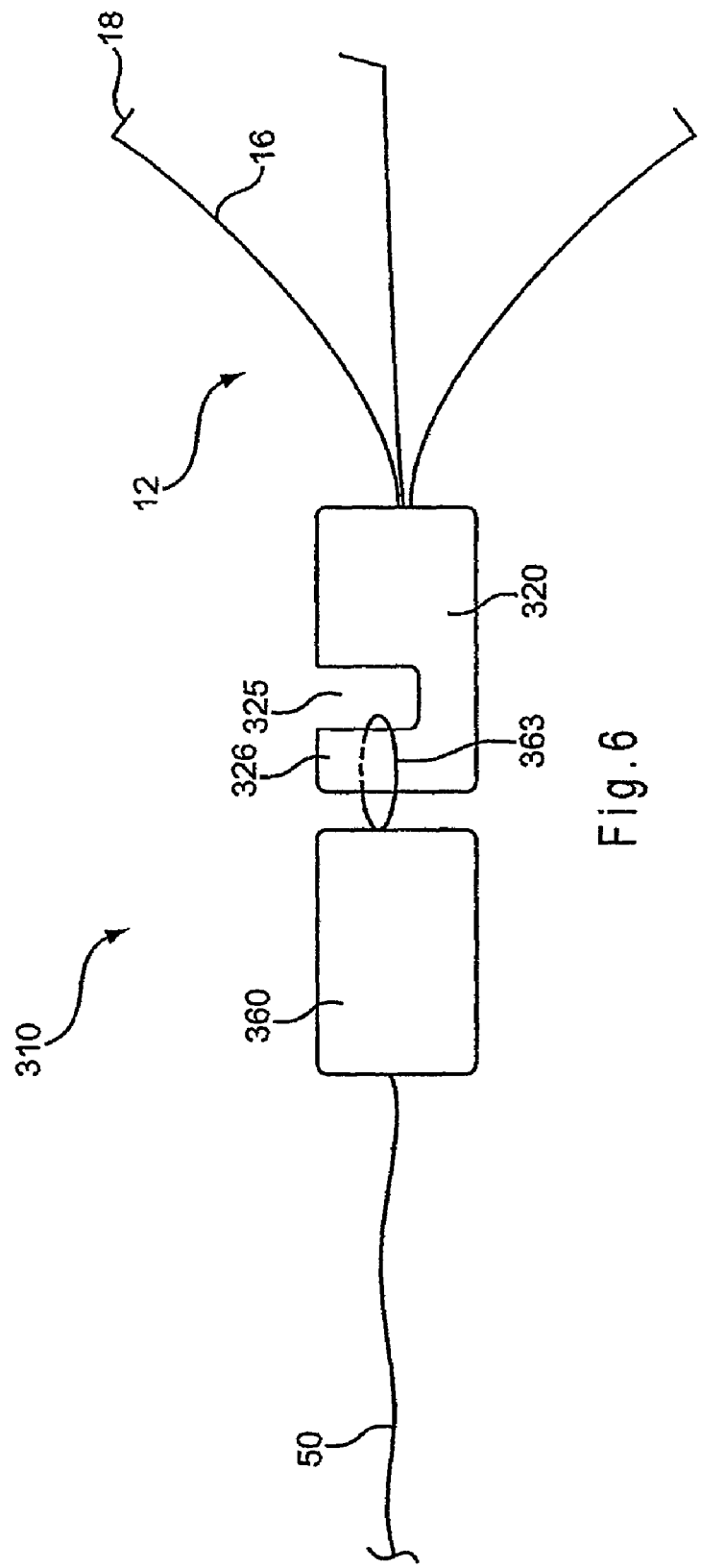
FIG. 6 is a side view of an alternative release mechanism that may be used to deploy a clip device.

Referring now to FIG. 6, a side view of a further alternative mechanism for deploying clip 12 is provided. Clip device 310 comprises first retainer 320 and second retainer 360, which are releasably secured together by loop member 363. For illustrative purposes, outer sheath 30, inner sheath 40, and sliding ring 70 are omitted from FIG. 6, although they preferably are provided in accordance with the embodiments described above. In this embodiment, first retainer 320 preferably comprises notch 325 formed therein and has hook member 326 disposed proximal to the notch, as shown in FIG. 6. Second retainer 360 has a proximal end attached to operating wire 50, and has a distal end having loop member 363 extending therefrom.

In operation, loop member 363 is placed over hook member 326, as shown in FIG. 6, thereby securely coupling first retainer 320 to second retainer 360. Sliding ring 70 is advanced over at least notch 325 to ensure that loop member 363 cannot be inadvertently detached. Clip device 310 then is advanced to a target site through a working channel of an endoscope, as generally described above. During deployment, outer sheath 30 is retracted proximally to expose clip 12 and permit radial expansion of arms 16. Inner sheath 40 is advanced distally to abut sliding ring 70, causing the sliding ring to be advanced distally towards clip 12 and causing the arms of clip 12 to close inward, as described above. Inner sheath 40 then is retracted proximally to uncover first retainer 320 and second retainer 360. At this time, loop member 363 is no longer radially constrained about hook member 326, which permits first retainer 320 to disengage from second retainer 360. The proximal face of hook member 326 can be angled to facilitate movement of loop member 363 out of notch 325. After the retainers have separated, all of the components (except clip 12 attached to first retainer 320) are removed through the working channel of the endoscope.

In an alternative embodiment to FIG. 6, second retainer 360 may be eliminated and operating wire 50 may comprise a loop member, i.e., similar to loop member 363, at its distal end. In this case, the loop member of operating wire 50 is directly coupled to hook member 326 of first retainer 320.

Referring now to FIGS. 7A-7B, a further alternative embodiment for releasably securing and deploying a clip device is provided. In FIG. 7A, clip device 410 comprises first retainer 420 and second retainer 460, which are releasably secured together by frangible element 418. The frangible element is designed to break apart in a controlled manner when a sufficient tensile force is imposed upon it, as explained in more detail below. In FIG. 7A, second retainer 460 is shown in the form of a cable that extends proximally within inner sheath 40. If desired, operating wire 50 may be coupled to a proximal region of second retainer 460 in a fashion similar to the other embodiments described above. Alternatively, second retainer 460 may be omitted and operating wire 50 may be coupled directly to first retainer 420, wherein operating wire 50 may comprise an integrally formed, frangible distal region.

Further, in this embodiment, clip 12' comprises three arms 16a, 16b and 16c having stop elements 97a, 97b and 97c, respectively. The stop elements preferably comprise a bead-shaped, oval-shaped, or circular-shaped metal material, or any other suitable shape. The stop elements may be disposed on an outer surface of one or more of arms 16a, 16b and 16c and soldered or otherwise attached proximal to ends 18 of the arms. Alternatively, the stop elements may be formed integrally with their respective arms during manufacture. Stop elements 97a, 97b and 97c serve multiple purposes. One purpose is to ensure that sliding ring 70' cannot be advanced over the distal end of clip 12'. Another purpose is to limit the amount of closing force that can be applied to arms 18 of clip 12'. Still another purpose of the stop elements is to engage distal end 475 of sliding ring 70' to facilitate disengagement of the first retainer from the second retainer, e.g., when retracting the second retainer with respect to the first retainer, or rotating the retainers with respect to each other, as explained more fully below.

When the stop elements are employed, distal end 475 of sliding ring 70' preferably comprises three channels 497a, 497b and 497c (see FIG. 7B) which are configured to permit movement of arms 16a, 16b and 16c therethrough, respectively. However, stop elements 97a, 97b and 97c are sized so that they cannot pass completely through the channels. Therefore, when sliding ring 70' is advanced distally over clip 12', arms 16a, 16b and 16c pass through channels 497a, 497b and 497c, respectively, but the stop elements serve as distal stop elements to ensure that the sliding ring cannot pass distally over the clip.

In a preferred embodiment, sliding ring 70' preferably comprises depressions 498a, 498b and 498c, which extend from the distal tip of sliding ring 70' into channels 497a, 497b and 497c, respectively (see FIG. 7B). Stop elements 97a, 97b and 97c preferably are sized to be at least partially seated within depressions 498a, 498b and 498c, respectively. In one embodiment, the stop elements may lockingly engage their respective depressions, e.g., using a snap-fit, thereby ensuring that sliding ring 70' cannot disengage from clip 12'.

In operation, clip device 410 is advanced to a target site through a working channel of an endoscope, as generally described above. The proximal end of first retainer 420 is coupled to the distal end of second retainer 460 using frangible element 418. During deployment, outer sheath 30 is retracted proximally to expose clip 12 and permit radial expansion of arms 16. Inner sheath 40 is advanced distally to abut sliding ring 70', causing the sliding ring to be advanced distally towards clip 12' and causing the arms of clip 12' to close inward, as described above. Stop elements 97a, 97b and 97c engage depressions 498a, 498b and 498c, respectively, to ensure that the sliding ring is not advanced distally past the end of the clip.

In a next step, inner sheath 40 is held steady while second retainer 460 (or operating wire 50 coupled to second retainer 460) is retracted proximally. The retraction of second retainer 460 with respect to first retainer 420 imposes a tensile force upon frangible element 418, thereby breaking the frangible element and detaching the retainers. Based on tactile feedback, a physician will be able to sense when the frangible element has been broken and the retainers have detached.

It should be noted that during proximal retraction of second retainer 460, clip 12' will be held steady and not displaced from engagement with the tissue. Specifically, after sliding ring 70' has been advanced distally and has engaged stop elements 97a, 97b and 97c, the stop elements prohibit proximal retraction of clip 12' with respect to sliding ring 70'. Since inner sheath 40 is held steady and prevents proximal retraction of sliding ring 70', clip 12' cannot be retracted proximally, either. This helps prevent excessive forces from being applied to the tissue.

Referring now to FIG. 8, a further alternative embodiment for releasably securing and deploying a clip, such as clip 12', is provided. In FIG. 8, clip 12' and sliding ring 70' preferably are provided as described in FIGS. 7A-7B above. Therefore, clip 12' comprises stop elements 97a, 97b and 97c, which are sized to be at least partially be seated within depressions 498a, 498b and 498c, respectively, at the distal end of sliding ring 70' (see FIG. 7B).

Clip device 510 comprises first retainer 520 and second retainer 560, which are releasably secured together by magnetic forces, i.e., first retainer 520 has a first magnetic force and second retainer 560 has an opposing magnetic force. In operation, inner sheath 40 is advanced distally to cause sliding ring 70' to close arms 16a, 16b and 16c. When sliding ring 70' is advanced distally, stop elements 97a, 97b and 97c of clip 12' engage the depressions in sliding ring 70'. Inner sheath 40 then is held steady while operating wire 50 is retracted proximally, thereby overcoming the magnetic force and causing second retainer 560 to detach from first retainer 520. In effect, distal end 564 of second retainer 560 separates from proximal end 522 of first retainer 520, and second retainer 560 becomes retracted further proximally within inner sheath 40. After the retainers have separated, inner sheath 40 is retracted proximally, and all of the components (except clip 12' attached to first retainer 520) are removed through the working channel of the endoscope.

Referring now to FIGS. 9A-9B, further alternative embodiments for deploying a clip, such as clip 12', are provided. In FIG. 9A, clip 12' and sliding ring 70' preferably are provided as described in FIGS. 7A-7B above. Therefore, clip 12' comprises stop elements 97a, 97b and 97c, which are sized to be at least partially be seated within depressions 498a, 498b and 498c, respectively, at the distal end of sliding ring 70' (see FIG. 7B).

Clip device 610 comprises first retainer 620 and second retainer 660, which are releasably secured together by a ball bearing and detent arrangement. Specifically, first retainer 620 has inner bore 627 formed in its proximal end. Ball elements 642 and 643 are coupled to opposing exterior regions of first retainer 620 and partially extend into bore 627, as shown in FIG. 9A. The ball elements also extend radially outward towards sliding ring 70', and preferably contact the sliding ring, as depicted in FIG. 9A. Ball elements 642 and 643 are movable, but not removable, relative to first retainer 620.

Second retainer 660 has an outer diameter that is less than the diameter of bore 627 of first retainer 620, thereby allowing second retainer 660 to be disposed within the bore. Second retainer 660 also has opposing notches 662 and 663 formed therein, which are sized to receive an outer portion of ball elements 642 and 643, respectively, as described below.

In operation, clip device 610 is advanced to a target site through a working channel of an endoscope, as generally described above. During advancement, sliding ring 70' and/or inner sheath 40 are disposed over ball elements 642 and 643, thereby urging the ball elements in an inward direction into a portion of notches 662 and 663, respectively. When urged radially inward towards the notches, ball elements 642 and 643 substantially prohibit longitudinal movement of first retainer 620 with respect to second retainer 660, as shown in FIG. 9A.

During deployment, outer sheath 30 is retracted proximally to expose clip 12' and permit radial expansion of arms 16. Inner sheath 40 is advanced distally to abut sliding ring 70', causing the sliding ring to be advanced distally towards clip 12' and causing the arms of clip 12' to close inward, as described above. Inner sheath 40 then is retracted proximally past second retainer 660. When sliding ring 70' and/or inner sheath 40 no longer constrain ball elements 642 and 643, the ball elements are permitted to move radially outward, i.e., out of notches 662 and 663. At this time, second retainer 660 may be retracted proximally via operating wire 50, and ball elements 642 and 643 will not catch on their respective detents. Alternatively, ball elements 642 and 643 may be deformable when subjected to a sufficient tensile release force.

The embodiment of FIG. 9B is similar to that described in FIG. 9A, with a main exception that one or more rivet elements 642' and 643' are employed in lieu of ball elements 642 and 643. Rivet element 642' preferably comprises a first end having flat surface 652 and a second end having enlarged rounded region 653. A smaller diameter portion extends between flat surface 652 and rounded region 653. The smaller diameter portion is disposed through a hole in first retainer 620', as shown in FIG. 9B, to contain rivet element 642'. In operation, when sliding ring 70' and/or inner sheath 40 are disposed over first retainer 620', rivet element 642' is urged radially inward, thereby urging rounded region 653 into notch 662' in second retainer 660' to secure the first retainer to the second retainer. When sliding ring 70' and/or inner sheath 40 no longer constrain rivet 642', it may move radially outward and will not catch on notch 662'. Therefore, second retainer 660' may disengage from first retainer 620'.

Referring now to FIGS. 10A-10B, variations on the embodiment described in FIGS. 9A-9B are shown. In FIG. 10A, clip device 710 preferably comprises two opposing ball elements 742 and 743 that selectively permit coupling of first retainer 720 and second retainer 760.

First retainer 720 has inner bore 727 formed in its proximal end, which is adapted to receive a reduced diameter distal region of second retainer 760, as shown in FIG. 10A. First retainer 720 further comprises first and second notches 722 and 723 formed in bore 727, while the distal region of second retainer 760 has recesses 762 and 763 formed therein. Recesses 762 and 763 are configured to contain a substantial portion of ball elements 742 and 743, respectively, while a portion of the ball elements may extend outside of the confines of the recesses, as depicted in FIG. 10A. The recesses are configured, however, to never permit the ball elements to escape therefrom.

In a preferred embodiment, biasing means 775, e.g., a compression spring, is disposed within recess 762. The biasing means is disposed beneath ball element 742 to bias the ball element radially outward, i.e., towards notch 722. A second biasing means (not shown) preferably is used to bias ball element 743 radially outward in the same manner.

In operation, clip device 710 is advanced to a target site through a working channel of an endoscope, as generally described above. During advancement, ball elements 742 and 743 are aligned with notches 722 and 723, respectively. The biasing means bias their respective ball elements radially outward into their respective notches to securely couple first retainer 720 to second retainer 760.

After deployment of clip 12', inner sheath 40 is advanced distally and held steady against sliding ring 70'. At this time, second retainer 760 may be retracted proximally via operating wire 50. Stop elements 97a, 97b and 97c may engage depressions 498a, 498b and 498c, respectively, in sliding ring 70' (see FIG. 7B). The intentional retraction of second retainer 760 by a physician will overcome the force provided by biasing means 775, thereby causing ball elements 742 and 743 to be forced radially inward and permitting disengagement of the two retainers. Alternatively, ball elements 742 and 743 may be deformable when subjected to a sufficient tensile release force. Once detached, second retainer 760 may be retracted via inner sheath 40, while first retainer 720 attached to clip 12' is left inside the patient.

The embodiment of FIG. 10B is similar to that described in FIG. 10A, with a main exception that one or more biased elements 742' and 743' are employed in lieu of ball elements 742 and 743. Biased elements 742' and 743' preferably are integrally formed with reduced diameter distal region 765 of second retainer 760', as shown in FIG. 10B. Biased elements 742' and 743' have a predetermined configuration in which they are biased radially outward into notches 722' and 723', respectively, to secure second retainer 760' to first retainer 720'. When it is desired to disengage the retainers, second retainer 760' is retracted proximally with respect to first retainer 720' to urge biased elements 742' and 743' radially inward, i.e., out of notches 722' and 723'. Therefore, second retainer 760' may disengage from first retainer 720'.

In the embodiments of FIGS. 9-10, it will be apparent that although two opposing ball elements are shown, only one ball element may be employed, or alternatively, three or more may be used. Additionally, while ball-shaped elements are depicted, it will be apparent that these elements may comprise other shapes, such as oval-shaped elements, cone-shaped elements, and so forth.

Referring now to FIGS. 11A-11B, a further alternative embodiment of the present invention is described. In FIGS. 11A-11B, clip 12' comprises stop elements 97a, 97b and 97c, which are sized to be at least partially be seated within depressions 498a, 498b and 498c, respectively, at distal end 475 of sliding ring 70' (see FIG. 7B). Clip device 810 comprises first retainer 820 and second retainer 860. First retainer 820 has bore 825 formed in its proximal end. Bore 825 has internal threading 827, which is configured to releasably mate with external threading 862, which is disposed on a distal region of second retainer 860. Torque cable 815 is coupled to a proximal region of second retainer 860 and preferably spans the entire length of the delivery system.

In the embodiment of FIGS. 11A-11B, inner sheath 40' and sliding ring 70'' are similar to the embodiments described above. However, the distal end of inner sheath 40' is configured to mate with the proximal end of sliding ring 70'' to inhibit rotational movement therebetween, for purposes explained below. In one embodiment, the distal end of inner sheath 40' comprises at least one notch 442 that is configured to mate with at least one corresponding knob 443 extending from the proximal end of sliding ring 70'', as shown in FIG. 11B.

In operation, clip device 810 is advanced to a target site through a working channel of an endoscope, as generally described above. During advancement, first retainer 820 is secured to second retainer 860 by engaging their respective internal and external threaded regions. After clip 12' is deployed, as described above, torque cable 815 is rotated in a direction that causes the threaded regions to disengage. Once the first and second retainers are disengaged, torque cable 815 and second retainer 860 may be retracted proximally via inner sheath 40', while first retainer 820 attached to clip 12' is left inside the patient.

In this particular embodiment, once sliding ring 70" has been advanced distally by inner sheath 40', stop elements 97a, 97b and 97c engage the depressions in sliding ring 70". As noted above, the stop elements may lock into engagement with the depressions in sliding ring 70", e.g., using a snap-fit. Further, notches 442 of inner sheath 40' mate with corresponding knobs 443 of sliding ring 70" (see FIG. 11B) to prevent rotational movement of the inner sheath with respect to the sliding ring. Therefore, by holding inner sheath 40' steady while rotating torque cable 815 relative thereto, second retainer 860 is rotated with respect to first retainer 820, thereby causing the retainers to disengage. In other words, by holding inner sheath 40' rotationally steady, sliding ring 70" cannot rotate (see FIG. 11B), and therefore, clip 12' cannot rotate because stop elements 97a, 97b and 97c are restrained within the depressions 498a, 498b and 498c of the rotationally-steady sliding ring.

Referring now to FIG. 12, a further alternative embodiment of the present invention is described. In FIG. 12, clip device 910 comprises first retainer 920 and second retainer 960. For illustrative purposes, the outer sheath, inner sheath, and sliding ring are omitted from FIG. 12. First retainer 920 has bore 925 formed in its proximal end, and further comprises first and second inwardly-directed knobs 927 and 928 projecting into bore 925, as shown in FIG. 12. Second retainer 960 has proximal and distal ends, and further has an outer diameter that is slightly smaller than an inner diameter of bore 925. Axial channels 967 and 968 are formed in the distal end of second retainer 960, preferably 180 degrees apart, and extend longitudinally from the distal end towards the proximal end, as shown in FIG. 12. Before reaching the proximal end, axial channel 967 transitions into circumferential channel 977, which preferably extends about 90 degrees around the outer circumference of second retainer 960. Similarly, axial channel 968 transitions into circumferential channel 978, which extends about 90 degrees around the outer circumference of second retainer 960, as shown in FIG. 12.

Channels 967, 968, 977 and 978 preferably are etched into an exterior surface of second retainer 960, which may be formed of stainless steel or the like. Knob 927 of first retainer 920 is sized for movement within channels 967 and 977, while knob 928 is sized for movement within channels 968 and 978, as described below.

In operation, clip device 910 is advanced to a target site through a working channel of an endoscope, as generally described above. During advancement, first retainer 920 is secured to second retainer 960 by aligning knobs 927 and 928 with axial channels 967 and 968, respectively. Second retainer 960 is moved towards first retainer 920 to cause the knobs to slide within their respective axial channels. When knobs 927 and 928 reach the proximal portion of their respective axial channels, second retainer 960 is rotated about 90 degrees with respect to first retainer 920, thereby causing knobs 927 and 928 to be advanced within their respective circumferential channels 977 and 978. In this state, first and second retainers 920 and 960 are coupled together, and longitudinal movement of the retainers with respect to each other is substantially prohibited.

Clip 12' may then be deployed and secured to tissue by advancing sliding ring 70" of FIG. 11B. In a next step, torque cable 915, which is operably coupled to the proximal end of second retainer 960, is rotated about 90 degree in a direction opposite the direction used to lock the retainers together. This rotation causes knobs 927 and 928 to be aligned with axial channels 967 and 968, respectively. At this time, second retainer 960 may be retracted proximally to cause knobs 927 and 928 to slide within axial channels 967 and 968, respectively, thereby unlocking the retainers. Once the first and second retainers are disengaged, torque cable 915 and second retainer 960 may be retracted proximally through inner sheath 40, while first retainer 920 attached to clip 12 is left inside the patient. It will be apparent that although two opposing knobs are shown in FIG. 12, only one knob/channel arrangement may be employed, or alternatively, three or more may be used.

In this embodiment, clip device 910 preferably employs clip 12', inner sheath 40' and sliding ring 70", as described in FIGS. 11A-11B above. As noted above, the use of such interlocking components will hold clip 12' rotationally stationary while second retainer 960 is rotated with respect to first retainer 920.

Referring now to FIGS. 13-17, various alternative embodiments of the present invention are described. Alternative clip 1012 comprises at least two arms, and in the embodiment of FIGS. 13A-13B, comprises three arms 1016a, 1016b and 1016c, each having proximal and distal ends. The distal ends of arms 1016a, 1016b and 1016c comprise bends 1018a, 1018b and 1018c, respectively, which are configured to engage tissue.

In general, clip 1012 is similar to clip 12, described above, with the main exception that arms 1016a, 1016b and 1016c comprise substantially flat regions along part or all of their length, as shown in FIGS. 13-13B. Moreover, the proximal ends of arms 1016a, 1016b and 1016c unite to form proximal end 1020 of clip 1012. Clip 1012 may be formed by cutting a flat clip having the desired number of arms (e.g., three) from a planar sheet of material, then bending the arms into the desired final shape. Proximal end 1020 has hole 1028 disposed therein, as shown in FIG. 13B. Optionally, at least one slit 1029 may be formed around the circumference of hole 1028, for purposes described below.

Referring now to FIG. 14, a first method of using clip 1012 of FIGS. 13A-13B is described. The apparatus comprises outer sheath 1030 and inner sheath 1040, which are similar to outer sheath 30 and inner sheath 40, as described above. The distal end of inner sheath 1040 is configured to engage collet 1070, which is disposed about the proximal end of clip 1012 and designed to close the clip, as explained below. Preferably, arms 1016a, 1016b and 1016c comprise distal stop members 1025a, 1025b and 1025c, as shown in FIG. 13A and FIG. 14. The distal stop members ensure that collet 1070 cannot be advanced distally over the clip. Collet 1070 is similar in design and function to sliding ring 70, 70' of the above-described embodiments.

In FIG. 14, clip 1012 is coupled to operating wire 1050 prior to deployment. The distal end of operating wire 1050 is coupled to frangible member 1052, which in turn is coupled to knob 1054, as shown in FIG. 14. Alternatively, frangible member 1052 may be integrally formed at the distal end of operating wire 1050. Frangible member 1052 extends through hole 1028 in proximal end 1020 of clip 1012, such that knob 1054 is confined distal to hole 1028, as shown in FIG. 14.

Clip 1012 is advanced to a target site with arms 1016a, 1016b and 1016c radially restrained by outer sheath 1030. Outer sheath 1030 is retracted to cause arms 1016a, 1016b and 1016c to deploy radially outward, as shown in FIG. 14 and generally described above. In a next step, inner sheath 1040 is advanced distally to abut collet 1070 and distally advance collet 1070 over arms 1016a, 1016b and 1016c. The arms are urged radially inward to engage tissue and promote hemostasis.

When collet 1070 abuts distal stop members 1025a, 1025b and 1025c, inner sheath 1040 is held steady while operating wire 1050 is retracted proximally. At this time, knob 1054 engages hole 1028 but cannot be pulled through the hole. The tensile force causes frangible member 1052 to break, thereby separating clip 1012 from operating wire 1050. The outer sheath, inner sheath and operating wire are then removed from the patient.

Figure 15:
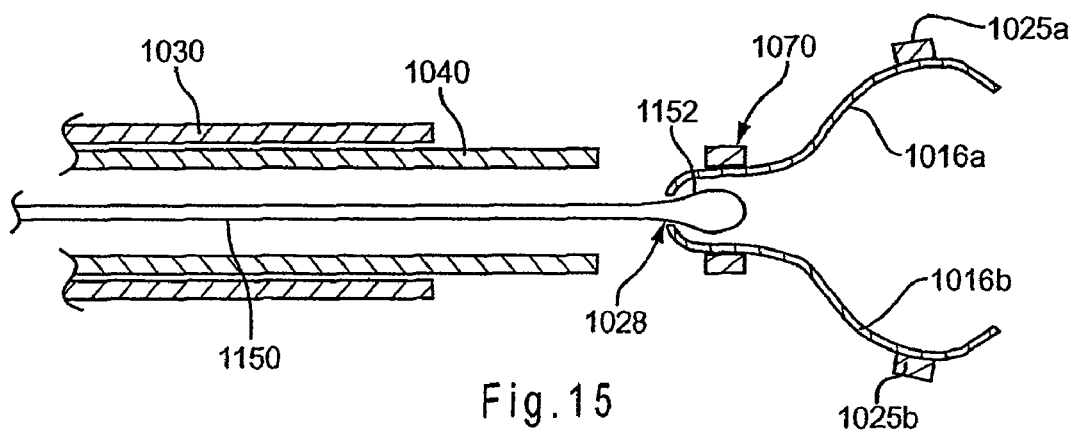
FIG. 15 is a side-sectional view illustrating an alternative method of deploying the clip of FIGS. 13A-13B.
Figure 16:
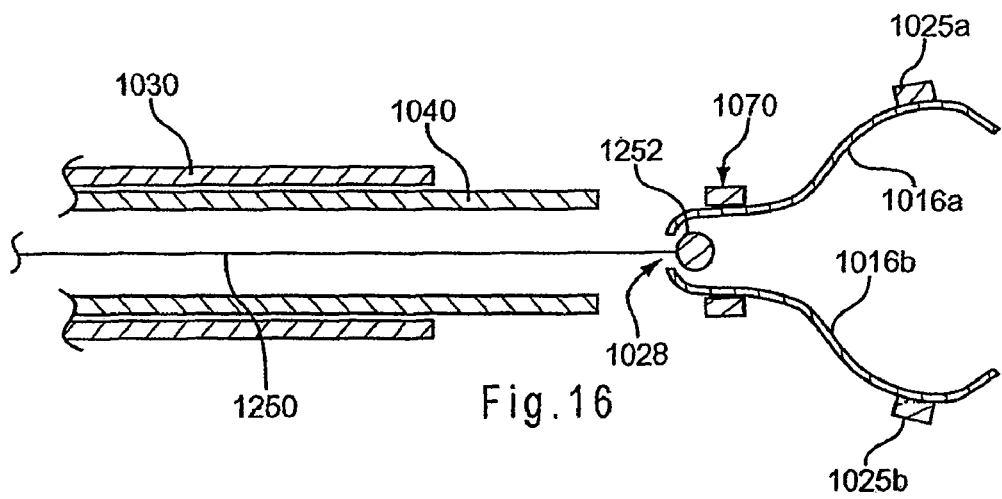
FIG. 16 is a side-sectional view illustrating an alternative method of deploying the clip of FIGS. 13A-13B.
Figure 17:
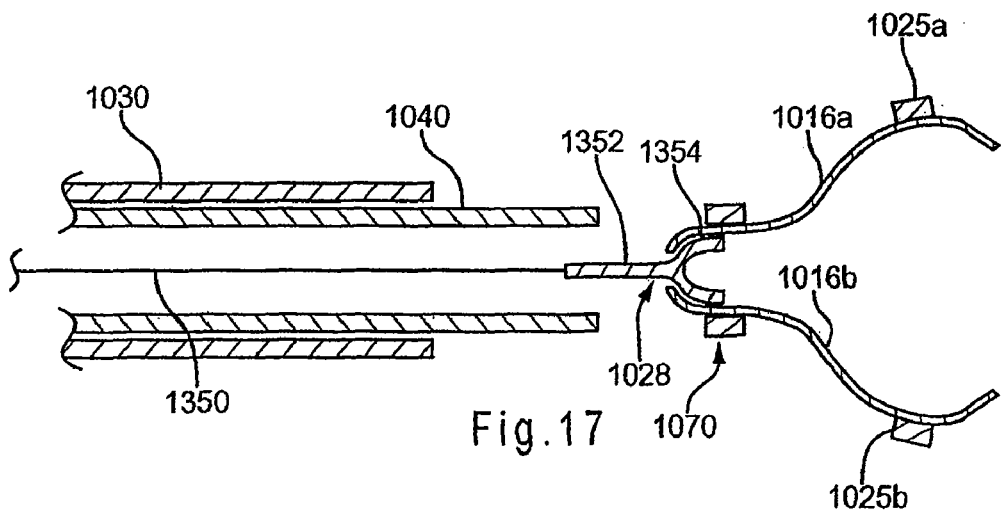
FIG. 17 is a side-sectional view illustrating an alternative method of deploying the clip of FIGS. 13A-13B.

Referring now to FIGS. 15-17, various alternative release mechanisms for deploying clip 1012 of FIGS. 13A-13B are described. In FIG. 15, wire 1150 is advanced distally through hole 1028 of clip 1012, then loop 1152 is formed, and wire 1150 is pulled back through hole 1028. In a relaxed state, loop 1152 is secured distal to hole 1028, i.e., the loop will not pull through the hole in the absence of a significant force. In use, collet 1070 is advanced via inner sheath 1040 and abuts distal stop members 1025a, 1025b and 1025c. Inner sheath 1040 then is held steady while wire 1150 is retracted proximally. At this time, an inwardly directed force causes loop 1152 to compress and pull through hole 1028, thereby separating clip 1012 from wire 1150.

In FIG. 16, the distal end of operating wire 1250 extends through hole 1028 and is coupled to knob 1252, which is disposed distal to hole 1028. In use, collet 1070 is advanced via inner sheath 1040 and abuts distal stop members 1025a, 1025b and 1025c. Inner sheath 1040 then is held steady while wire 1250 is retracted proximally. At this time, knob 1252 pulls through hole 1028, thereby separating clip 1012 from operating wire 1050. Preferably, in this embodiment, at least one slit 1029 (see FIG. 13B) is employed to facilitate retraction of knob 1252 through hole 1028.

In FIG. 17, the distal end of operating wire 1350 is coupled to deformable member 1354. In this example, deformable member 1354 comprises at least two arms that extend radially outward in a relaxed state. The arms of deformable member 1354 may be coupled to rigid proximal section 1352, which in turn is coupled to operating wire 1350, as shown in FIG. 17. Alternatively, operating wire 1350 may be coupled directly to deformable member 1354.

In use, proximal section 1352 (or operating wire 1350) or is disposed through hole 1028, while deformable member 1354 is disposed distal to hole 1028, as shown in FIG. 17. Collet 1070 is advanced via inner sheath 1040 and abuts distal stop members 1025a, 1025b and 1025c, and inner sheath 1040 then is held steady while operating wire 1350 is retracted proximally. At this time, the arms of deformable member 1354 are urged radially inward to pull deformable member 1354 through hole 1028, thereby separating clip 1012 from operating wire 1350. In this embodiment, at least one slit 1029 (see FIG. 13B) may be employed to facilitate retraction of deformable member 1354 through hole 1028.

Figure 18A:
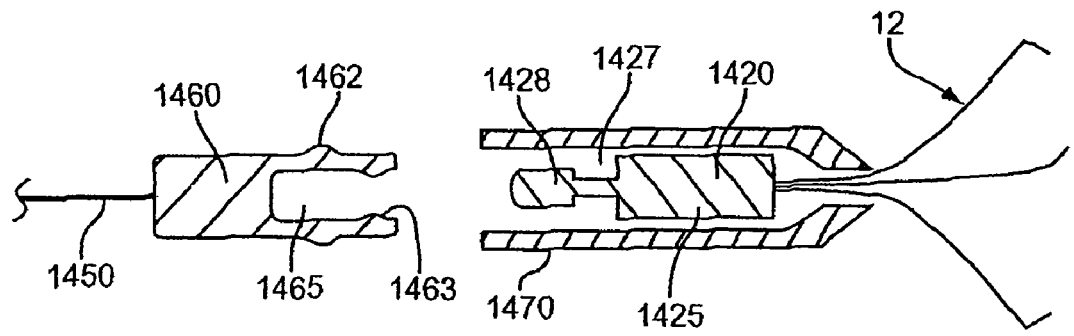
FIGS. 18A-18C are side-sectional views illustrating an alternative retainer system.
Figure 18B:
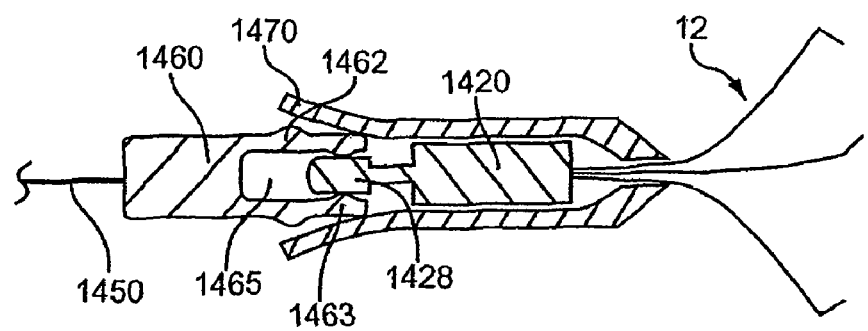
Figure 18C:
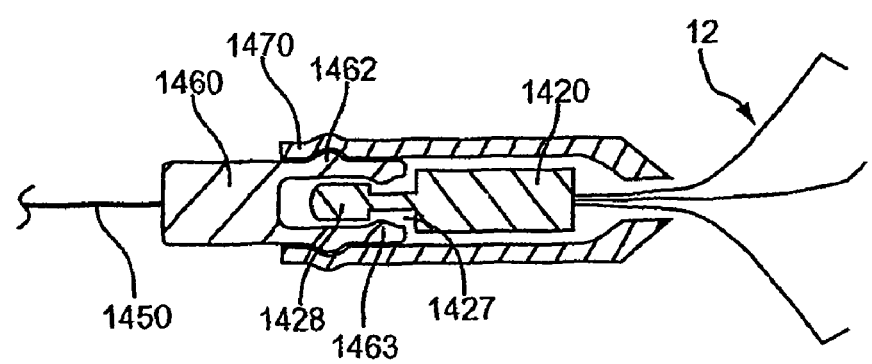

Referring now to FIGS. 18A-18C, a further alternative clip retainer system is shown. First retainer 1420 has proximal and distal regions 1428 and 1425. Distal region 1425 comprises a generally cylindrical shape and is attached to clip 12. Proximal region 1428 preferably has a smaller diameter than distal region 1425, and may comprise a rounded proximal edge, as depicted in FIG. 18A. At least one notch 1427 is disposed between the proximal and distal regions, as shown in FIG. 18A.

Second retainer 1460 comprises a generally cylindrical body having proximal and distal regions. The proximal region is attached to operating wire 1450. The distal region comprises bore 1465 having at least one knob 1463 extending therein, as shown in FIG. 18A. Further, an exterior surface of second retainer 1460 has at least one protruding member 1462 extending radially outward, as depicted in FIG. 18A.

In the embodiment of FIGS. 18A-18C, sliding ring 1470 is disposed over first retainer 1420, as shown in FIG. 18A. Sliding ring 1470 comprises a flexible proximal region, as will be explained in FIG. 18B. Optionally, sliding ring 1470 may comprise a lateral slit (not shown) disposed on a proximal region to enhance its radial flexibility and accommodate second retainer 1460, as explained below.

In operation, a physician may attach second retainer 1460 to first retainer 1420 by distally advancing second retainer 1460. As shown in FIG. 18B, protruding member 1462 causes radial expansion of a proximal region of sliding ring 1470. At this time, knob 1463 is passed over proximal region 1428 of first retainer 1420, preferably with little or no resistance. As second retainer 1460 is further advanced, proximal region 1428 of first retainer 1420 is disposed within the confines of bore 1465. Moreover, this placement allows sliding ring 1470 to exert a resilient inward force upon protruding member 1462, thereby urging knob 1463 into notch 1427, as shown in FIG. 18C.

In a next step, an inner and outer sheath may be disposed over the apparatus and inserted into the patient, as generally set forth above. After the inner sheath advances sliding ring 1470 in a distal direction to close the arms of clip 12, second retainer 1460 may be retracted proximally via operating wire 1450 to allow knob 1463 to disengage from notch 1427, thereby separating the retainers.

Figure 19:
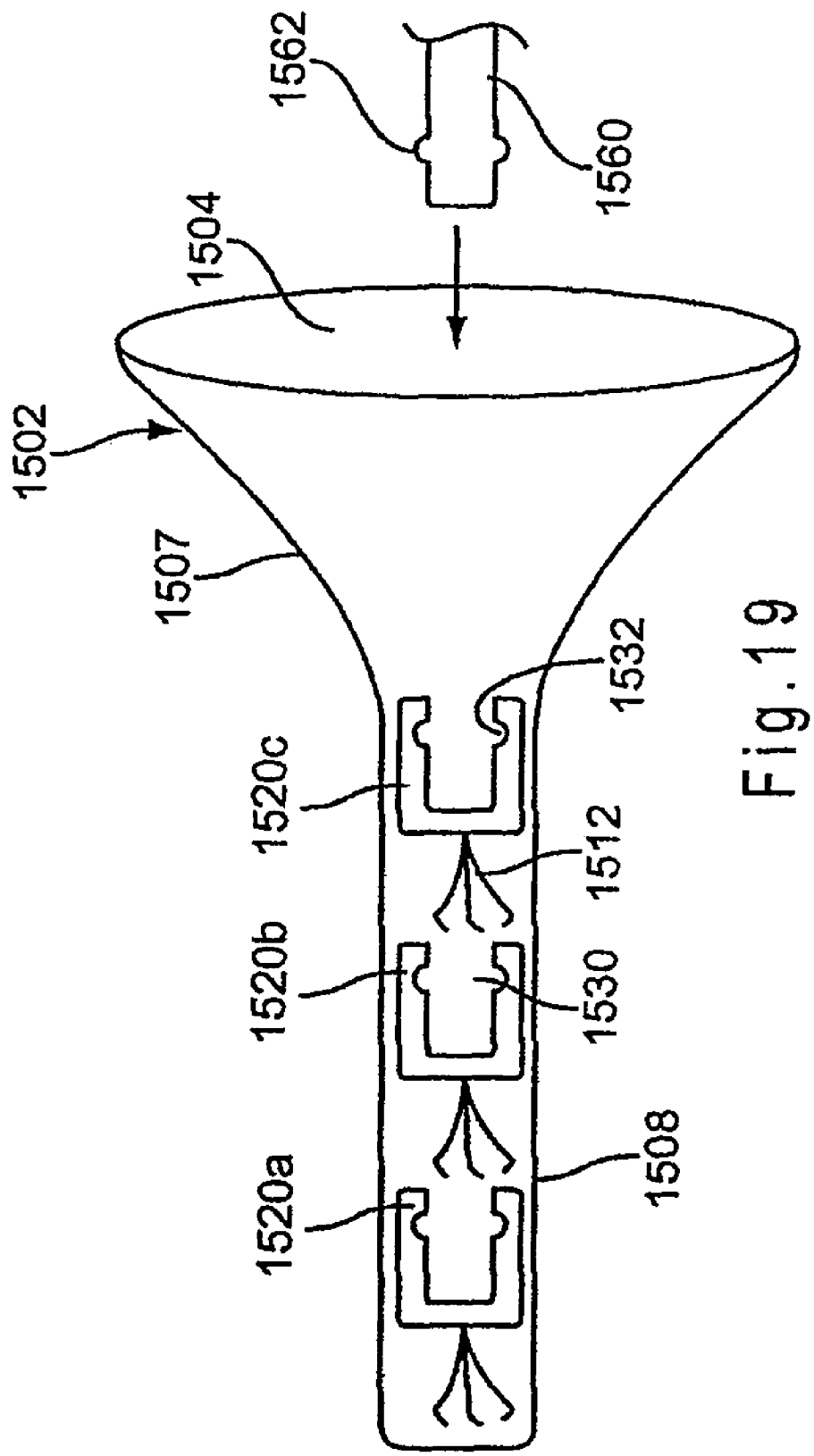
FIG. 19 is a side-sectional view illustrating a clip retaining apparatus.

Referring now to FIG. 19, an apparatus that may be used to hold multiple clips is disclosed. Clip holder 1502 comprises proximal region 1508 and enlarged diameter distal region 1504. A taper 1507 is provided between the proximal and distal regions. Multiple clips 1520a, 1520b and 1520c are adapted to be pre-loaded into proximal region 1508, as shown in FIG. 19. The arms 1512 of clips 1520a-c may be nested within bores 1530 of adjacent clips, or disposed proximal to adjacent clips as shown. First retainers 1520a-c may comprise portions adapted to mate with complementary portions on second retainer 1560. For example, ball element 1562 may be adapted to engage with notch elements 1532 of second retainers 1520a-c. Advantageously, each time a new clip is needed, a physician may simply insert second retainer 1560 into clip holder 1502, engage a clip, and proceed to deploy the clip within a patient according the steps generally set forth above.

Figure 20:
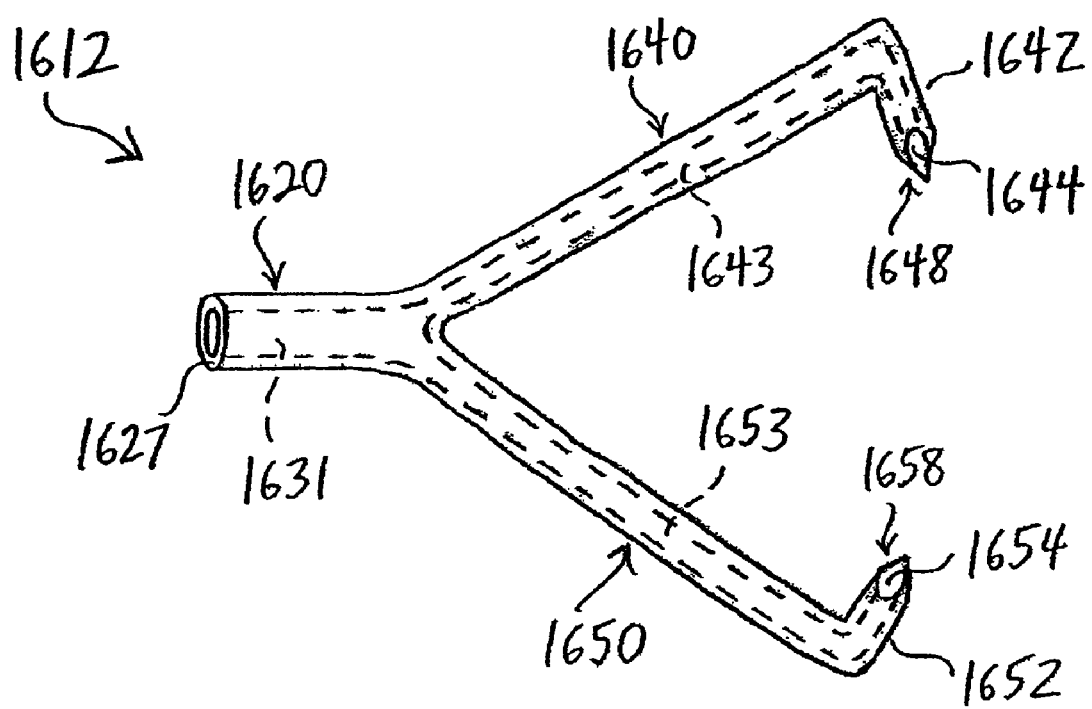
FIG. 20 is a side view of an alternative embodiment of a clip configured to deliver a sclerosing agent.
Figure 21:
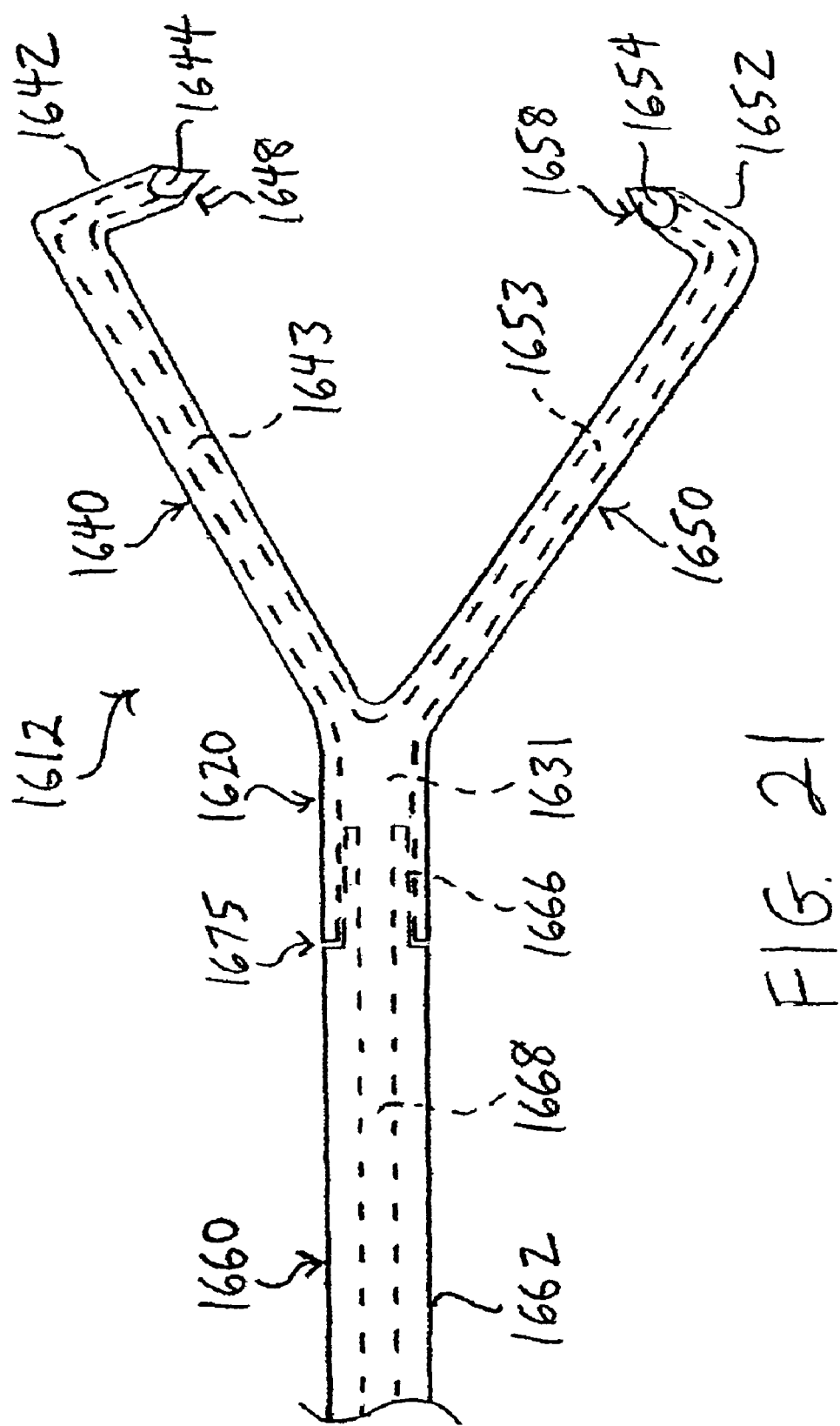
FIG. 21 is a side view of a retaining system that may be used in conjunction with the embodiment of FIG. 20.

Referring now to FIGS. 20-21, a further alternative embodiment is described. In FIG. 20, clip 1612 comprises plurality of arms 1640 and 1650, each having proximal and distal ends. The proximal ends of arms 1640 and 1650 preferably are coupled to, or integrally formed with, first retainer 1620, as depicted in FIG. 20. The distal ends of arms 1640 and 1650 preferably are bent radially inward at regions 1642 and 1652, respectively, to better grasp tissue and facilitate hemostasis. Moreover, a portion of the distal ends of arms 1640 and 1650 may be beveled to form sharpened tips 1648 and 1658, respectively, as shown in FIG. 20. While two arms 1640 and 1650 are depicted in FIGS. 20-21, it will be apparent that clip 1612 may employ a greater number of arms.

In this embodiment, arm 1640 comprises lumen 1643, which spans from the proximal end to the distal end of arm 1640, as shown in FIG. 20. Similarly, arm 1650 comprises lumen 1653, which spans from the proximal end to the distal end of arm 1650. Lumens 1643 and 1653 are in fluid communication with lumen 1631 of first retainer 1620. More specifically, lumen 1643 of arm 1640 provides fluid communication between lumen 1631 of first retainer 1620 and outlet bore 1644 in sharpened tip 1648. Similarly, lumen 1653 of arm 1650 provides fluid communication between lumen 1631 of first retainer 1620 and outlet bore 1654 in sharpened tip 1658, as depicted in FIG. 20.

While there are numerous manufacturing techniques possible, clip 12 may be manufactured by injection molding techniques to form first retainer 1620 that branches into plurality of arms 1640 and 1650. The beveled edges of sharpened tips 1648 and 1658 may be formed after the molding technique. Exemplary dimensions for plurality of arms 1640 and 1650 include an outer diameter of about 0.025 inches, an inner diameter of about 0.013 inches, and a wall thickness of about 0.012 inches. Exemplary dimensions for first retainer 1620 include an outer diameter of about 0.08 inches, an inner diameter of about 0.07 inches, and a wall thickness of about 0.01 inches. These exemplary dimensions are used for reference purposes and are not intended to be limiting.

In accordance with one aspect, clip 1612 is configured to provide mechanical clipping therapy and injection sclerotherapy to facilitate hemostasis of gastrointestinal bleeding. As explained in greater detail below, clip 1612 may be deployed such that sharpened tips 1648 and 1658 engage tissue and provide for a mechanical closure to promote healing of damaged tissue, such as ulcers. Additionally, a sclerosing agent may be injected through outlet bores 1644 and 1654 in the sharpened tips via lumens 1643 and 1653, respectively. This allows for the direct provision of such agents to underlying bleeding, for example, if a clot has formed beneath the mucosal layer of tissue. While numerous suitable sclerosing agents may be used in conjunction with clip 1612, some exemplary agents include absolute alcohol, morrhuate sodium, sodium tetradecyl sulfate, polydoconol, sotrodecol, ethanolamine oleate, aethoxysclerol, and cyanoacrylates such as histoacryl.

Referring now to FIG. 21, an exemplary retainer system for deploying clip 1612 and facilitating delivery of a sclerosing agent is shown. In FIG. 21, second retainer 1660 comprises proximal and distal regions 1662 and 1666. Lumen 1668 is disposed within second retainer 1660 and spans between proximal and distal regions 1662 and 1666. Lumen 1668 preferably extends to the proximal end of the delivery system and terminates at a port (not shown) through which the sclerosing agent can be injected.

Proximal region 1662 comprises a first outer diameter and distal region 1666 preferably comprises a second outer diameter smaller than the first outer diameter, thereby allowing distal region 1666 to be disposed within lumen 1631 of first retainer 1620, as shown in FIG. 21. Proximal region 1662 of second retainer 1660 may abut proximal end 1627 of first retainer 1620. As depicted in FIG. 21, the outer diameter of proximal region 1662 of second retainer 1660 preferably is substantially identical to the outer diameter of first retainer 1620, thereby providing a substantially flush exterior surface.

When second retainer 1660 is joined to first retainer 1620 as shown in FIG. 21, lumen 1668 is placed in fluid communication with lumen 1631, which in turn is placed in fluid communication with lumens 1643 and 1653 of plurality of arms 1640 and 1650, respectively. Therefore, the injection of a fluid, such as a sclerosing agent, via lumen 1668 will achieve injection of the fluid through outlet bores 1644 and 1654 in the sharpened tips. In one embodiment, a sclerosing agent injection port (not shown) may be coupled to the proximal end of the second retainer 1660, thereby placing the sclerosing agent injection port in fluid communication with the lumen 1668 of the second retainer 1660.

Many of the coupling mechanisms described in FIGS. 1-12 above may be used in conjunction with clip 1612 to couple second retainer 1660 to first retainer 1620, while maintaining fluid communication between lumen 1668 of second retainer 1660 and lumen 1631 of first retainer 1620. For example, lumen 1631 of first retainer 1620 may have internal threading that is configured to releasably mate with external threading on distal region 1666 of second retainer 1660, in the manner that internal threading 827 mates with external threading 862, as explained in the embodiment of FIGS. 11A-11B above. If a threaded engagement is employed, inner sheath 40' and sliding ring 70" may be employed to deliver and deploy clip 1612, in the manner explained in FIGS. 11A-11B above. Moreover, arms 1640 and 1650 of clip 1612 may comprise stop elements 97a, 97b and 97c, which are sized to be at least partially be seated within depressions 498a, 498b and 498c, respectively, at distal end 475 of sliding ring 70' (see FIG. 7B).

Clip 1612 may be delivered and deployed to engage tissue to promote hemostasis using any suitable manner described hereinabove. For example, in one embodiment, clip 1612 is advanced to a target site through a working channel of an endoscope. During advancement, first retainer 1620 is secured to second retainer 1660, for example, by engaging respective internal and external threaded regions. Clip 1612 may be deployed in the manner described above, i.e., using inner sheath 40' and sliding ring 70", to cause plurality of arms 1640 and 1650 to engage tissue. Upon distal advancement of sliding ring 70", sharpened tips 1648 and 1658 mechanically engage the tissue to promote hemostasis.

In a next step, a sclerosing agent may be injected through the sclerosing agent injection port. The sclerosing agent then flows through lumen 1668, and subsequently may flow through lumens 1631, 1643 and 1653. The sclerosing agent then flows through outlet bores 1644 and 1654 in the sharpened tips to access underlying bleeding, for example, if a clot has formed beneath the mucosal layer of tissue. Advantageously, using this technique, the bleeding may be treated both mechanically via the engagement of plurality of arms 1640 and 1650 with the tissue, and further by the injection of the sclerosing agent through the lumens in plurality of arms 1640 and 1650.

After clip 1612 is deployed and the desired fluid injection is achieved, proximal region 1662 of second retainer 1660 is rotated in a direction that causes the threaded regions of first and second retainers 1620 and 1660 to disengage. Once the first and second retainers are disengaged, second retainer 1660 may be retracted proximally via inner sheath 40', while first retainer 1620 attached to clip 1612 is left inside the patient.

Optionally, a sealing member may be provided to reduce the likelihood of the sclerosing agent leaking during injection of the agent. For example, an O-ring may be placed over distal region 1666 of second retainer 1660 at junction 1675, such that the O-ring abuts both proximal region 1662 of second retainer 1660 and proximal end 1627 of first retainer 1620, thereby forming a substantially fluid-tight seal therebetween.

Further, after injection of the sclerosing agent to the desired site, and prior to the step of disengaging second retainer 1660 from first retainer 1620, a suction source optionally may be used to aspirate remaining fluid in clip 1612 to reduce the likelihood of having any excess sclerosing agent leak after disengagement of the retainers. In this embodiment, the suction source may be coupled to a proximal port and placed in fluid communication with lumen 1668. The sclerosing agent is injected through lumen 1668, and flows through lumens 1631, 1643 and 1653. After a sufficient amount of sclerosing agent has been injected to the desired site, and optionally after a sufficient time has elapsed, the suction source may be activated to aspirate remaining fluid in lumens 1668, 1631, 1643 and 1653. Subsequently, second retainer 1660 is disengaged from first retainer 1620. Using this technique, the amount of sclerosing agent that leaks from the system may be reduced.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

I claim:

1. A clip device for use in endoscopic medical procedures comprising:
a clip having a plurality of arms each having a proximal end and a distal end, wherein the proximal end of each of the arms is joined to a first retainer and extends distally therefrom, wherein each of the arms are spaced apart from each other when the clip is in an open position and adjacent to each other when the clip is in a closed position;
at least one lumen disposed within at least a first of the plurality of arms, wherein the lumen spans from the proximal end to the distal end of the first arm; and
at least one outlet bore formed in the distal end of the first arm,
wherein the distal ends of the plurality of arms are adapted to engage tissue in the closed position, and wherein a sclerosing agent is adapted to be delivered to the tissue via the lumen and the outlet bore in the first arm wherein the first retainer comprises a lumen formed therein, the lumen of the first retainer being in fluid communication with the lumen disposed within the first of the plurality of arms, and further comprising a second retainer adapted to be coupled to the first retainer, wherein the first retainer is configured to be coupled to the second retainer prior to deployment of the clip, and wherein the first retainer is configured to be disengaged from the second retainer after the clip is deployed.

2. The clip device of claim 1 wherein each of the plurality of arms comprises at least one lumen formed therein that spans from the proximal end to the distal end of each respective arm.

3. The clip device of claim 1 wherein the distal ends of the plurality of arms are bent radially inward to facilitate grasping of the tissue.

4. The clip device of claim 1 wherein the distal ends of each of the plurality of arms are beveled to form a sharpened tip.

5. The clip device of claim 1 wherein the second retainer comprises at least one lumen formed therein, wherein the lumen of the second retainer is adapted to be placed in fluid communication with the lumen of the first retainer when the second retainer is coupled to the first retainer.

6. The clip device of claim 1 wherein the second retainer comprises proximal and distal regions, wherein an outer diameter of the distal region is smaller than an outer diameter of the proximal region, and wherein the distal region is adapted to be disposed within the lumen of the first retainer.

7. The clip device of claim 1 further comprising:
internal threading disposed in the lumen of the first retainer; and
external threading disposed on the distal region of the second retainer and configured to engage the internal threading, wherein rotation of the second retainer causes the external threading to disengage from the internal threading.

8. A clip device for use in endoscopic medical procedures comprising:
a clip having a plurality of arms each having a proximal end and a distal end, wherein the proximal end of each of the arms is joined to a first retainer and extends distally therefrom;
a lumen disposed within at least a first of the plurality of arms, wherein the lumen spans from the proximal end to the distal end of the first arm; and
a second retainer adapted to be coupled to the first retainer prior to deployment of the clip, wherein the second retainer is configured to be disengaged from the first retainer after the clip is deployed,
wherein the first retainer and the second retainer each comprise a lumen formed therein, the lumens of the first and second retainers being in fluid communication with the lumen disposed within the first arm for delivering a sclerosing agent to a tissue site after the first arm engages the tissue site.

9. The clip device of claim 8 wherein each of the arms are formed of a resilient material and shaped so that the distal ends tend to be spaced apart from each other when the clip is in an open position and adjacent to each other when the clip is in a closed position.

10. The clip device of claim 8 wherein each of the plurality of arms comprises a lumen formed therein that spans from the proximal end to the distal end of each respective arm.

11. The clip device of claim 8 wherein the distal ends of the plurality of arms are bent radially inward to facilitate grasping of the tissue site.

12. The clip device of claim 8 wherein the distal ends of each of the plurality of arms are beveled to form a sharpened tip.

13. The clip device of claim 8 wherein the second retainer comprises proximal and distal regions, wherein an outer diameter of the distal region is smaller than an outer diameter of the proximal region, wherein the distal region is adapted to be disposed within the lumen of the first retainer.

14. The clip device of claim 13 further comprising:
internal threading disposed in the lumen of the first retainer; and
external threading disposed on the distal region of the second retainer and configured to engage the internal threading, wherein rotation of the second retainer causes the external threading to disengage from the internal threading.

* * * * *